(12) United States Patent
Lim et al.

(10) Patent No.: US 11,911,519 B2
(45) Date of Patent: Feb. 27, 2024

(54) DEVICE FOR PRODUCING NANO PARTICLES AND PREPARATION METHOD OF NANO PARTICLES USING THE SAME

(71) Applicants: SOONCHUNHYANG UNIVERSITY INDUSTRY ACADEMY COOPERATION FOUNDATION, Asan-si (KR); KOREA INSTITUTE OF CERAMIC ENGINEERING AND TECHNOLOGY, Jinju-Si (KR)

(72) Inventors: Jong Min Lim, Cheonan-si (KR); Daekyung Sung, Sejong-si (KR); Won II Choi, Seoul (KR); Hyeon Woo Han, Seoul (KR); Sehee Jeong, Cheonan-si (KR); Yoonhee Na, Incheon (KR); Jiseob Woo, Cheongju-si (KR)

(73) Assignees: SOONCHUNHYANG UNIVERSITY INDUSTRY ACADEMY COOPERATION FOUNDATION, Asan-si (KR); KOREA INSTITUTE OF CERAMIC ENGINEERING AND TECHNOLOGY, Jinju-si (KR)

( * ) Notice: Subject to any disclaimer, the term of this patent is extended or adjusted under 35 U.S.C. 154(b) by 436 days.

(21) Appl. No.: 17/150,037

(22) Filed: Jan. 15, 2021

(65) Prior Publication Data
US 2022/0211635 A1    Jul. 7, 2022

(30) Foreign Application Priority Data
Jan. 5, 2021    (KR) .......................... 10-2021-0000798

(51) Int. Cl.
*A61K 9/00*    (2006.01)
*A61K 9/51*    (2006.01)
(Continued)

(52) U.S. Cl.
CPC .......... *A61K 9/5192* (2013.01); *A61K 9/5123* (2013.01); *B01F 23/451* (2022.01);
(Continued)

(58) Field of Classification Search
CPC ..................... A61K 9/5192; B01F 2101/2204
See application file for complete search history.

(56) References Cited

U.S. PATENT DOCUMENTS

| 2013/0122058 A1 | 5/2013 | Chow et al. |
| 2013/0184641 A1* | 7/2013 | Li .......................... A61M 5/172 604/67 |

(Continued)

FOREIGN PATENT DOCUMENTS

| JP | 2018-197392 A | 12/2018 |
| KR | 10-2013-0109736 A | 10/2013 |

OTHER PUBLICATIONS

Rohit Karnik et al., "Microfluidic Platform for Controlled Synthesis of Polymeric Nanoparticles", NANO Letters, 2008, pp. 2906-2912, vol. 8, No. 9.

(Continued)

*Primary Examiner* — Anshu Bhatia
(74) *Attorney, Agent, or Firm* — Sughrue Mion, PLLC

(57) ABSTRACT

A device for producing nanoparticles includes: a first connector comprising a first supply tube fitting member, a second supply tube fitting member, and a first discharge tube fitting member; a first tube having one side connected to the first supply tube fitting member; a second tube having one side connected to the second supply tube fitting member; a first conduit having one side connected to the first discharge tube fitting member; a first supply connected to another side of the first tube to supply a first material to the first conduit; and a second supply connected to another side of the second tube to supply a second material to the first conduit.

10 Claims, 25 Drawing Sheets

(51) Int. Cl.
  B01F 23/40 (2022.01)
  B01F 23/451 (2022.01)
  B01F 25/31 (2022.01)
  B01F 35/71 (2022.01)
  C07F 15/02 (2006.01)
  F16L 41/02 (2006.01)
  F16L 41/03 (2006.01)
  B01F 25/00 (2022.01)
  B01F 101/00 (2022.01)

(52) U.S. Cl.
  CPC ............ B01F 23/49 (2022.01); B01F 25/311 (2022.01); B01F 35/71761 (2022.01); C07F 15/02 (2013.01); F16L 41/021 (2013.01); F16L 41/03 (2013.01); *B01F 2025/916* (2022.01); *B01F 2101/2204* (2022.01); *B01F 2215/0459* (2013.01)

(56) References Cited

U.S. PATENT DOCUMENTS

2014/0135708 A1* 5/2014 Pryce Lewis ...... A61M 5/31511
                                                          604/222
2021/0220289 A1* 7/2021 Coffman .............. A61K 9/1688

OTHER PUBLICATIONS

Jong-Min Lim et al., "Ultra-High Throughput Synthesis of Nanoparticles with Homogeneous Size Distribution Using a Coaxial Turbulent Jet Mixer", ACS Nano, 2014, pp. 6056-6065, 8, 6.

Hyeon Woo Han, "Continuous Production of Polystyrene Nanoparticles with Improved Dispersion Stability Using a Coaxial Turbulent Jet Mixer", Creative Commons, Commons Deed, Feb. 15, 2020, 66 pages.

Jong-Min Lim, "Fabrication of functional micro/nano hybrid particles using microfluidic device", Soonchunhyang University, Mar. 27, 2020.

\* cited by examiner

DEVICE FOR PRODUCING NANO PARTICLES AND PREPARATION METHOD OF NANO PARTICLES USING THE SAME

CROSS-REFERENCE TO RELATED APPLICATION

This application claims priority under 35 U.S.C. § 119 to Korean Patent Application No. 10-2021-0000798, filed on Jan. 5, 2021, in the Korean Intellectual Property Office (KIPO), the disclosure of which is incorporated by reference herein in its entirety.

TECHNICAL FIELD

Embodiments of the present disclosure relate to a device for producing nanoparticles and a method for producing nanoparticles using the same.

DISCUSSION OF RELATED ART

Although nanoparticles have the same composition, their physical properties may vary according to their size or shape. Since nanotechnology is utilized in various fields, various studies are being conducted to synthesize nanoparticles having a uniform shape and size.

As an example of conventional methods for preparing polymer nanoparticles, there is a batch process such as emulsion polymerization and dispersion polymerization. In the batch process, polymer nanoparticles are synthesized from pure monomers through a polymer polymerization process. However, the polymer polymerization used in the batch process requires a long time reaction using very pure chemical materials (monomer, initiator, etc.) through complex and sophisticated reaction process control, and when the conventional batch process is scaled-up for mass production, it takes a lot of time and money to optimize the operating conditions again.

As another example of conventional methods for preparing polymer nanoparticles, there is a nanoprecipitation scheme in which a polymer is introduced into a non-solvent to generate nanoparticles by self-assembly of the polymer. In the nanoprecipitation method, since a polymer rather than a monomer is used as a precursor of nanoparticles, the process is relatively simple, and relatively uniform nanoparticles may be synthesized even with low-purity and inexpensive chemicals. However, it is difficult to precisely control a mixing process, so the uniformity of the nanoparticles is low. In addition, in the case of mass production of nanoparticles by the conventional batch process, the stability is poor, and the size distribution of the nanoparticles may not be maintained over time, making the mass production difficult to apply. In addition, there is a limitation in reproducibility between batches, and when the conventional batch process is scaled-up for mass production, it takes a lot of time and money to optimize the operating conditions again.

In order to overcome the limitations of the batch process, a method of continuously preparing uniform nanoparticles using a microfluidic device has been developed. Microfluidic devices are prepared using photolithography and replica molding schemes, and nanoparticles are self-assembled through precise control of a solution in the microfluidic device (Nanoletters 2008, 8, 2906, Adv. Mater 2011, 23, H79). This nanoprecipitation method using a microfluidic device may produce more uniform nanoparticles, as compared to a batch-type bulk nanoprecipitation method, and the size of the nanoparticles may be controlled by changing operating conditions such as flow rate. However, because a size of a microfluidic channel is very small, an amount of nanoparticles produced per hour is very small, making it difficult to apply to industrial applications.

In order to overcome the limitations of the batch process, a method of continuously preparing uniform nanoparticles using flash nanoprecipitation has been developed. In this method, dissimilar to the conventional batch process in which uniform nanoparticles are produced from monomers through polymer polymerization, a precursor solution is prepared by dissolving a polymer in a solvent, and the precursor solution is rapidly mixed with a non-solvent to self-assemble uniform nanoparticles. The present inventors have previously been able to produce uniform nanoparticles by making a hole in a T-shaped tube fitting, inserting a needle thereto, and fixing the needle with an adhesive (ACS Nano 2014, 8, 6056). In such a case, however, alignment of a coaxial tube was difficult, the precursor solution leaked due to physical/chemical damage to bonding portions, and particles synthesized by reaction of the precursor material with the non-solvent were precipitated on device walls, thus contaminating the device. In addition, since a syringe pump was used, continuous production was difficult and the flow rate could not be adjusted. In addition, the nanoparticles have a uniform size distribution immediately after production, but dispersion stability in an aqueous solution is poor, so there is a problem that aggregation is formed when stored for a long time or when centrifuged.

RELATED ART

Patent Art (Patent Document 1) Korean Patent Publication KR 10-2013-0109736
(Patent Document 2) US Patent Publication US 2013/0122058 A1
(Non-Patent Document 1) Nanoletters 2008, 8, 2906, Adv. Mater 2011, 23, H79
(Non-Patent Document 2) ACS Nano 2014, 8, 6, pp. 6056-6065

It is to be understood that this background of the technology section is intended to provide useful background for understanding the technology and as such disclosed herein, the technology background section may include ideas, concepts or recognitions that were not part of what was known or appreciated by those skilled in the pertinent art prior to a corresponding effective filing date of subject matter disclosed herein.

SUMMARY

Embodiments of the present disclosure is directed to a device for producing nanoparticles improved in that a solution may not leak when a reactant is injected into a mixer, the reactant may be continuously injected into the mixer, safety may be ensured even for highly toxic materials, and high reproducibility and enhanced particle uniformity may be provided because the reactants are mixed in a turbulent state.

According to an embodiment, a device 100 for producing nanoparticles includes a first connector 110 including a first supply 141 tube fitting member 111, a second supply 142 tube fitting member 112, and a first discharge tube fitting member 114; a first tube 121 having one side connected to the first supply 141 tube fitting member 111; a second tube 122 having one side connected to the second supply 142 tube fitting member 112; a first conduit 130 having one side connected to the first discharge tube fitting member 114; a first supply 141 connected to another side of the first tube 121 to supply a first material to the first conduit 130; and a second supply 142 connected to another side of the second tube 122 to supply a second material to the first conduit 130. At least a portion of the first tube 121 or the second tube 122 is disposed in the first connector 110 and in the first conduit 130, an outer diameter of the at least a portion of the first tube 121 or the second tube 122 disposed in the first conduit 130 is smaller than an inner diameter of the first conduit 130, a length of the at least a portion of the first tube 121 or the second tube 122 disposed in the first conduit 130 is shorter than a length of the first conduit 130, and a material of the first connector 110, the first tube 121, the second tube 122 and the first conduit 130 includes a fluorine-based polymer.

In some embodiments, in the device 100 for producing nanoparticles, the first supply 141 or the second supply 142 may be a diaphragm pump.

In some embodiments, in the device 100 for producing nanoparticles, the first connector 110 may further include a third supply 143 tube fitting member 113, and the device 100 for producing nanoparticles may further include: a third tube 123 having one side connected to the third supply 143 tube fitting member 113; and a third supply 143 connected to another side of the third tube 123 to supply a third material to the first conduit 130.

In some embodiments, the device 100 for producing nanoparticles may further include: a second connector 210 including a connection tube fitting member 211, a fourth supply 242 tube fitting member 212, and a second discharge tube fitting member 213; the first conduit 130 having one side connected to the connection tube fitting member 211; a fourth tube 222 having one side connected to the fourth supply 242 tube fitting member 212; a second conduit 230 having one side connected to the second discharge tube fitting member 213; and a fourth supply 242 connected to another side of the fourth tube 222 to supply a fourth material to the second conduit 230. A material of the second connector 210, the fourth tube 222, and the second conduit 230 may include a fluorine-based polymer.

In some embodiments, in the device 100 for producing nanoparticles, the first supply 141 may supply the first material to the first conduit 130 to form turbulence at an end portion of the at least a portion of the first tube 121 in the first conduit 130, or the second supply 142 may supply the second material to the first conduit 130 to form turbulence at an end portion of the at least a portion of the second tube 122 in the first conduit 130.

In some embodiments, in the device 100 for producing nanoparticles, the first material and the second material may be mixed while forming turbulence in the first conduit 130.

In some embodiments, in the device 100 for producing nanoparticles, a Reynolds number of a solution flow of a mixture of the first material and the second material may be 800 or more.

In some embodiments, the nanoparticles formed by the device 100 for producing nanoparticles may be formed at a rate of 20 mg/min or more.

In some embodiments, in the device 100 for producing nanoparticles, the first material may include a nano-precursor, and the second material may include a non-solvent.

In some embodiments, in the device 100 for producing nanoparticles, the third material may include a nano-precursor, a non-solvent, a quenching material, or a surfactant.

In some embodiments, in the device 100 for producing nanoparticles, the produced nanoparticles may include at least one of: polystyrene, PLGA-PEG, gold, silver, silica, disulfide, iron oxide, siRNA/PEI, lipid vesicles, drug molecules, fluorescent molecules, reactive oxygen species (ROS)-reactive drug delivery nanoparticles.

The foregoing is illustrative only and is not intended to be in any way limiting. In addition to the illustrative aspects, embodiments and features described above, further aspects, embodiments and features will become another by reference to the drawings and the following detailed description.

DETAILED DESCRIPTION

Embodiments will now be described more fully hereinafter with reference to the accompanying drawings. Although the invention may be modified in various manners and have several embodiments, embodiments are illustrated in the accompanying drawings and will be mainly described in the specification. However, the scope of embodiments is not limited to the embodiments and should be construed as including all the changes, equivalents and substitutions included in the spirit and scope according to an embodiment.

Expressions such as "including" as used herein are to be understood as open-ended terms including the possibility of including other embodiments.

The terms "preferable" and "preferably" used herein are not intended to exclude other embodiments from the scope of the present disclosure.

Each of steps may take place in a different order than the specified order unless the context clearly indicates a specific order.

All technical terms used in this specification have meanings that are generally understood by those of ordinary skill in the technical field to which the present disclosure belongs.

Figure 1:
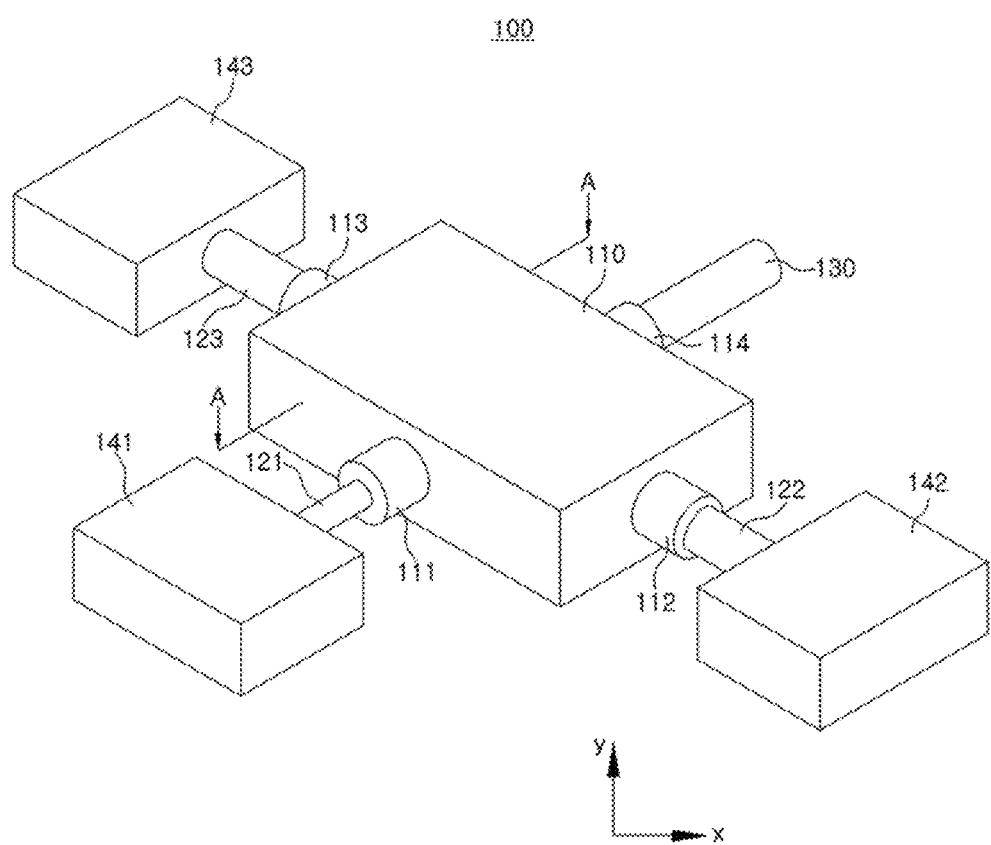
FIG. 1 illustrates a device 100 for producing nanoparticles according to an embodiment of the present disclosure.
Figure 2:
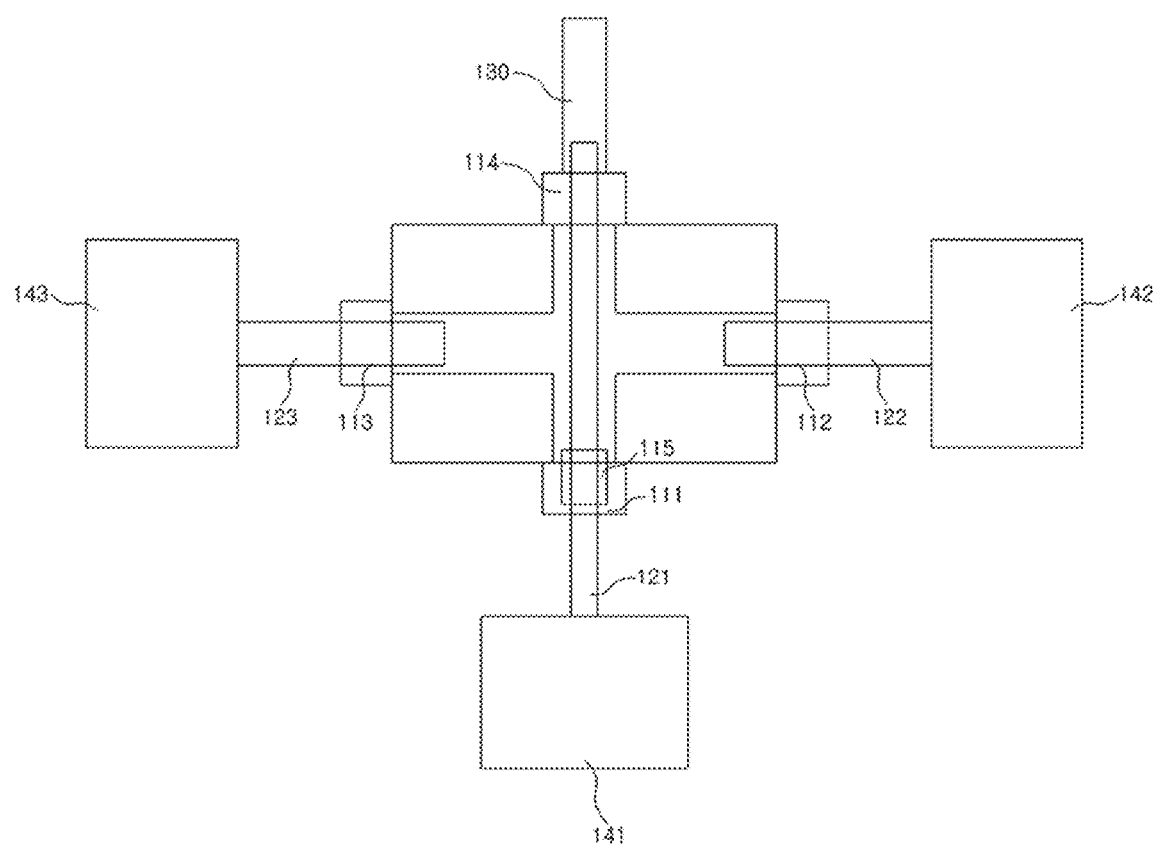
FIG. 2 is a cross-sectional view illustrating a device 100 for producing nanoparticles according to an embodiment of the present disclosure.

A device 100 for producing nanoparticles according to an embodiment of the present disclosure includes a first connector 110; a first tube 121; a second tube 122; a first conduit 130; a first supply 141; and a second supply 142 (FIGS. 1 and 2).

The first connector 110 is not particularly limited in terms of its shape as long as the first tube 121, the second tube 122, and the first conduit 130 may be connected thereto. In addition, since two or more tubes may be further connected to the first connector 110, there is no particular limitation on the shape as long as three or more tubes and the first conduit 130 may be connected thereto. For example, when viewed on an x-y axis, the shape may be a right-angled surface, for example, T-shaped or cross-shaped, or may be a round circle without a right-angled surface.

The first connector 110 includes a first supply tube fitting member 111, a second supply tube fitting member 112, and a first discharge tube fitting member 114. Each of the tube fitting members connects the first connector 110 to the tube and to the first conduit 130. Conventionally, when supplying a reactant to a conduit through a connector, an upper portion of the connector was drilled, and the reactant was supplied to the conduit by inserting a needle thereto. For this reason, even though the needle was fixed with an adhesive, the solution may leak. However, according to an embodiment of the present disclosure, since the tube and the first conduit 130 are fixed to the first connector 110 by using the tube fitting member, the reactant may not be leaked and it is safe from toxic reactants during manufacture. In addition, since the device 100 for producing nanoparticles is manufactured by assembling only the tubes and fittings, it may be manufactured faster and more conveniently than conventional devices.

The first tube 121 and the second tube 122 allow a first material or a second material, which are to be a reactant such as a nano-precursor or an anti-solvent, to reach the first conduit 130 from the first supply 141 and the second supply 142 trough the first connector 110. A shape of the tube may be a right-angled pillar, such as a triangular pillar or a quadrangular pillar, or may have a cylindrical shape. In addition, a thickness of the tube may be less than 5%, less than 10%, less than 20%, less than 30%, less than 40%, less than 50%, less than 60%, less than 70%, less than 80%, or less than 90% of a total cross-sectional area of the tube. The size and uniformity of the formed nanoparticles may be controlled by adjusting the shape or thickness of the tube.

One side of the first tube 121 is connected to the first supply tube fitting member 111, and one side of the second tube 122 is connected to the second supply tube fitting member 112. One of opposite end portions of each tube is an injection portion into which the reactant such as a nano-precursor or an anti-solvent is injected from the supply. The other one of the opposite end portions of each tube is a discharge portion through which the injected reactant moves and is discharged to the first connector 110. In such an embodiment, as described above, the tube and the first connector 110 are connected to each other by the tube fitting member.

The first conduit 130 is a place which the reactant such as a nano-precursor or an anti-solvent reaches through the first tube 121 or the second tube 122. Each of the reactants is mixed at this reaching portion to form nanoparticles. In such an embodiment, when turbulence is formed at the reaching portion, a production amount of the formed nanoparticles may increase. More specific details will be described below.

One side of the first conduit 130 is connected to the first discharge tube fitting member 114. One of opposite end portions of the first conduit 130 is an injection portion through which the reactants supplied from the supply and discharged to the first connector 110 through the first tube 121 and the second tube 122 are supplied. The other of the opposite end portions of the first conduit 130 is a discharge portion through which nanoparticles formed by mixing of the injected reactants are discharged. In such an embodiment, as described above, the first conduit 130 and the first connector 110 are connected to each other by the tube fitting member.

The first supply 141 and the second supply 142 may supply the first material or the second material, which is to become the reactant such as a nano-precursor or an anti-solvent, to the first tube 121 or the second tube 122, respectively, such that they may reach the first conduit 130 through the first connector 110. The first supply 141 is connected to another side of the first tube 121 to supply the first material to the first conduit 130, and the second supply 142 is connected to another side of the second tube 122 to supply the second material to the first conduit 130. The first material and the second material supplied to the first conduit 130 are mixed in the first conduit 130, thereby forming nanoparticles. As such, it is possible to precisely control physicochemical properties of the nanoparticles by changing fluid flow through the supply. As an example, when the reactant is supplied to the first conduit 130 by varying a flow rate of the reactant flowing in the first conduit 130 through the supply, size and uniformity of the formed nanoparticles may change.

On the other hand, in the case of using a syringe pump as the supply, since a solution is injected through the above-described syringe, it may be difficult to continuously produce nanoparticles. This is because once all the solution in the syringe is used, the syringe should be changed again. Accordingly, it may be more desirable to use a pump capable of continuously supplying the reactant from the supply to the tube. As examples of such a pump, a diaphragm pump, a smoothie pump, a plunger pump, a hydraulic bypass pump, a solenoid pump, a drum pump or a magnet pump may be used, and most preferably, a diaphragm pump may be used. In an example of using a diaphragm pump as the supply, a reservoir of the diaphragm is continuously replenished with solution. A pulsation damper may be used to reduce pulsation during solution injection.

At least a portion of the first tube 121 or the second tube 122 is disposed in the first connector 110 and in the first conduit 130. Since at least a portion of the tube through which the reactant moves is disposed in the first conduit 130, when the reactant including the nano-precursor encounters the anti-solvent, it does not contact surfaces of a wall of the device. Conventionally, in the case of using a nanoprecipitation method to manufacture nanoparticles, the nano-precursor solution and the anti-solvent meet each other, and nanoparticles are precipitated on the device wall. Accordingly, there was a problem that the device is contaminated, the efficiency is low, and the device needs to be replaced when used for a long time. However, in the case of using the device 100 for producing nanoparticles according to an embodiment of the present disclosure, although the nano-precursor solution and the anti-solvent meet each other, a precipitate is prevented from adhering to the device.

In addition, since at least a portion of the tube through which the reactant moves is disposed in the first conduit 130, the reactant may be directly supplied into the first conduit 130. Otherwise, the reactant may be supplied to the first connector 110 to flow therethrough to the first conduit 130.

An outer diameter of a portion of the first tube 121 or the second tube 122 disposed in the first conduit 130 is smaller than an inner diameter of the first conduit 130. More specifically, the outer diameter of the tube may be 90% or less, 80% or less, 70% or less, 60% or less, 50% or less, 40% or less, 30% or less, 20% or less, or 10% or less of the inner diameter of the first conduit 130. In addition, a length of a portion of the first tube 121 or the second tube 122 disposed in the first conduit 130 is shorter than a length of the first conduit 130. Accordingly, the reactants may be mixed in the first conduit 130 to form nanoparticles.

Materials of the first connector 110, the first tube 121, the second tube 122, and the first conduit 130 include a fluorine-based polymer. If a syringe pump is used as the supply, the syringe may break because a glass syringe should be used. In addition, when a capillary tube connected from the syringe pump to the first connector 110 is made of glass, it is more fragile, and when a toxic material is used as the reactant, there may be a safety problem. On the other hand, the device 100 for producing nanoparticles according to an embodiment of the present disclosure includes an inert fluorine-based polymer material in all parts of the device 100 that may contact the solution, for example, the supply, the first connector 110, the tube, and the first conduit 130, and accordingly, it is safe. As an example, when a diaphragm pump is used as the supply, a fluorine-based polymer material is used for all parts of the diaphragm pump that the solution may contact. As an example of such a fluorine-based polymer, fluorinated ethylene propylene (FEP), ethylene tetrafluoroethylene (ETFE), polytetrafluoroethylene (PTFE), polyvinylidene fluoride (PVDF), polyvinylfluoride (PVF), polychlorotrifluoroethylene (PCTFE), perfluoroalkoxy polymer (PFA), ethylenechlorotrifluoroethylene (ECTFE), or perfluoropolyether (PFPE) may be used, and most preferably, ETFE and FEP may be used.

In the device 100 for producing nanoparticles according to an embodiment of the present disclosure, the first supply 141 or the second supply 142 may be a diaphragm pump.

The diaphragm pump is a type of pump that pumps up and discharges liquid by vertical motion of a pump membrane, and is usually used for fuel pumps of gasoline engines. As described above, rather than using a syringe pump to prepare nanoparticles, nanoparticles may be more continuously formed by applying a diaphragm pump. A pulsation damper may be used to reduce pulsation during solution injection.

In the device 100 for producing nanoparticles according to an embodiment of the present disclosure, the first connector 110 may further include a third supply tube fitting member 113, and may further include a third tube 123 having one side connected to the third supply tube fitting member 113 and a third supply 143 connected to another side of the third tube 123 to supply a third material to the first conduit 130. The third supply tube fitting member 113 connects the first connector 110 and the third tube 123. The third tube 123 allows a third material, which is to become the reactant such as a nano-precursor or an anti-solvent, to reach the first conduit 130 from the third supply 143 through the first connector 110. According to an embodiment of the present disclosure, the reactant flows through the third tube 123, and the third tube 123 is connected to the tube fitting member, so that the reactant does not leak. The third supply 143 supplies the third material, which is to become the reactant such as a nano-precursor or an anti-solvent, to the third tube 123 such that it may reach the first conduit 130 through the first connector 110. The third supply 143 is connected to another side of the third tube 123 to supply the third material to the first conduit 130. The third supply 143 is not limited as long as it is a pump capable of continuously supplying the third material to the first conduit 130, and most preferably, may be a diaphragm pump. The third material may be a material such as a nano-precursor or an anti-solvent, and may be a nano-precursor the same as or different from the first material; an anti-solvent, a surfactant, or a quenching material the same as or different from the second material; or any other material that may react. Since the device 100 for producing nanoparticles according to an embodiment of the present disclosure uses a tube fitting member, it is possible to additionally connect a tube, and thus the above-described third material may be injected.

Figure 3:
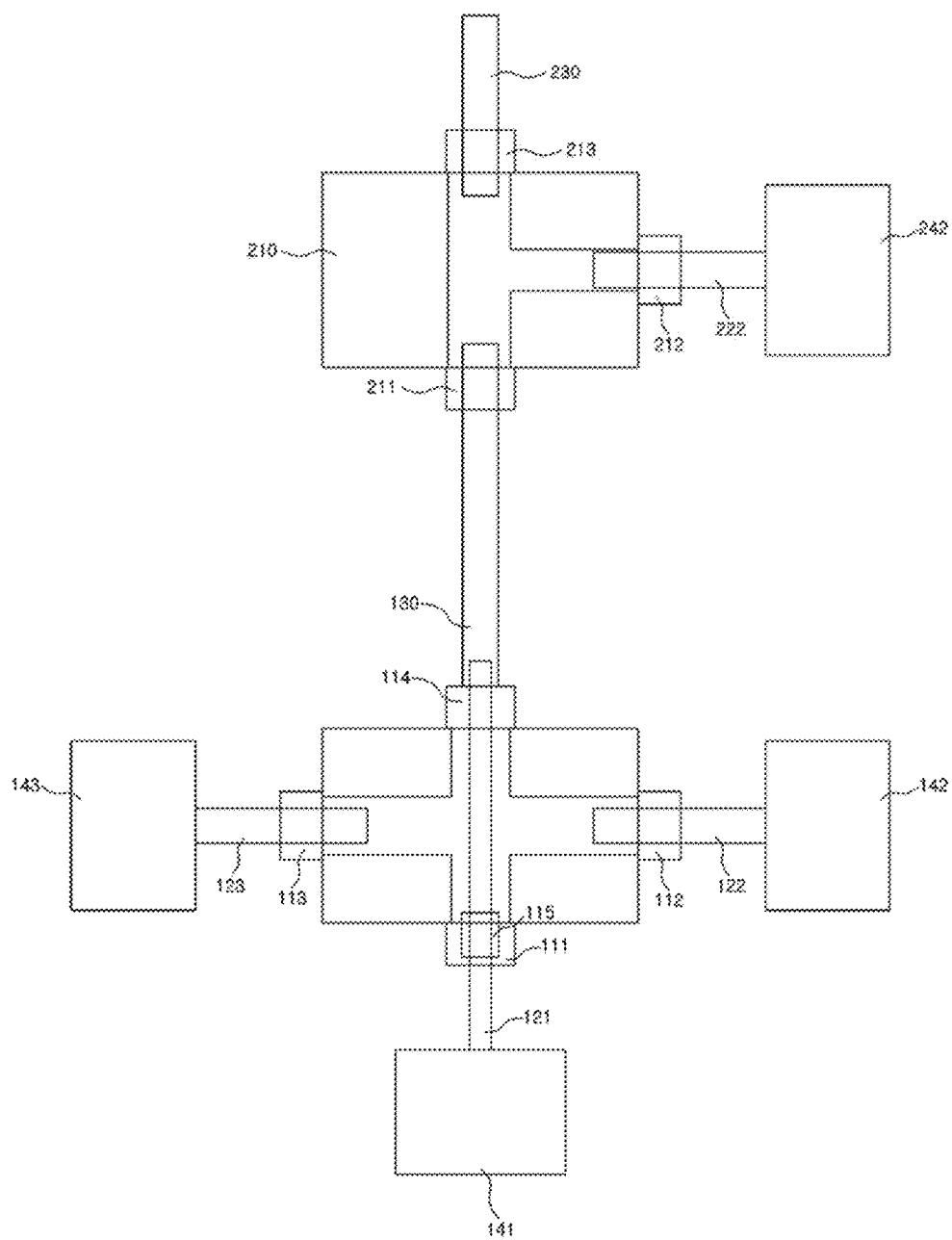
FIG. 3 is a cross-sectional view illustrating a device 100 for producing nanoparticles according to an embodiment of the present disclosure.

The device 100 for producing nanoparticles according to an embodiment of the present disclosure may further include a second connector 210 including a connection tube fitting member 211, a fourth supply tube fitting member 212, and a second discharge tube fitting member 213; the first conduit 130 having one side connected to the connection tube fitting member 211; a fourth tube 222 having one side connected to the fourth supply tube fitting member 212; a second conduit 230 having one side connected to the second discharge tube fitting member 213; and a fourth supply 242 connected to another side of the fourth tube 222 to supply a fourth material to the second conduit 230, and a material of the second connector 210, the fourth tube 222, and the second conduit 230 may further include a fluorine-based polymer (FIG. 3).

Since the device 100 for producing nanoparticles according to an embodiment of the present disclosure uses a tube fitting member, it is possible to additionally connect a tube, so that the fourth material may be injected. As the aforementioned components are further added, it is possible to further react the fourth material with a mixture or reacted material of the first material with the second material or with a mixture or reacted material of the first material, the second material and the third material. The fourth material may be a material such as a nano-precursor or an anti-solvent, and may be a nano-precursor the same as or different from the first material; an anti-solvent, a surfactant, or a quenching material the same as or different from the second material, and any other material that may react.

According to an embodiment of the present disclosure, the reactant flows through the fourth tube 222, and the reactant does not leak because the fourth tube 222 is connected to the tube fitting member. The fourth supply 242 supplies the fourth material, which is to become the reactant such as a nano-precursor or an anti-solvent, to the fourth tube 222 such that the fourth material may reach the second conduit 230 through the second connector 210. The fourth supply 242 is connected to another side of the fourth tube 222 to supply the fourth material to the second conduit 230. The fourth supply 242 is not limited as long as it is a pump capable of continuously supplying the fourth material to the second conduit 230, and most preferably, may be a diaphragm pump.

Other details of the second connector and various fitting members, tubes, conduits, and supplies connected thereto include all descriptions of various fitting members, tubes, conduits, and supplies connected to the first connector 110.

In addition, a fifth material, a sixth material, and the like may be supplied in the same manner as a manner in which the first to fourth materials are supplied, and the number of supplied materials is not limited.

In the device 100 for producing nanoparticles according to an embodiment of the present disclosure, the first tube 121 and the second tube 122 may be vertically connected to the first connector 110 (FIG. 1). However, there is no limit to the connection angle, for example, it may be 10°, 20°, 30°, 40°, 50°, 60°, 70°, or 80°. In addition, in the device 100 for producing nanoparticles according to an embodiment of the present disclosure, the first tube 121 and the second tube 122 may be connected to the first connector 110 in a line (FIG. 3). However, there is no limit to the connection angle, for example, it may be 100°, 110°, 120°, 130°, 140°, 150°, 160°, 170°, or 180°. When connected in a line, not only a portion of the first tube 121 is disposed in the first connector 110 and the first conduit 130, but also a portion of the second tube 121 is disposed in the first connector 110 and the first conduit 130 as well.

In the device 100 for producing nanoparticles according to an embodiment of the present disclosure, the first supply 141 may supply the first material to the first conduit 130 so that turbulence is formed at an end portion of the at least a portion of the first tube 121 in the first conduit 130, or the second supply 142 may supply the second material to the first conduit 130 so that turbulence is formed at an end portion of the at least a portion of the second tube 122 in the first conduit 130. As used herein, turbulence refers to an irregular flow of fluid, and is a concept that contrasts with laminar flow, which is a regular flow. Turbulence may include vortex and jets. Conventionally, since materials were mixed by diffusion in a first conduit 130, the flow rate was slow and the production amount was small. In addition, the reaction time was long, and thus the size of produced particles was large, and the particles were not uniform. However, in the device 100 for producing nanoparticles according to an embodiment of the present disclosure, since materials are mixed in a turbulent state such as a jet flow, the production amount of nanoparticles is large, the size of the nanoparticles is small, and they are uniform.

As such, nanoparticles may be produced using the device 100 for producing nanoparticles described above.

A method of producing nanoparticles includes continuously supplying the first material and the second material to the first conduit 130 using the first supply 141 and the second supply 142; mixing the first material and the second material in the first conduit 130; and forming nanoparticles by mixing the first material and the second material in the first conduit 130.

The continuously supplying of the first material and the second material to the first conduit 130 by using the first supply 141 and the second supply 142 is as described above.

The continuously supplying of the first material and the second material may further include continuously supplying the third material to the first conduit 130 using the third supply 143, as described.

The continuously supplying of the first material and the second material may further include continuously supplying the fourth material to the second conduit 230 using the fourth supply 242, as described. In addition, the fifth material, the sixth material, and the like may be supplied in the same manner as in the supplying of the first to fourth materials, and the number of supplied materials is not limited.

The first material may include a nano-precursor, and the second material may include an anti-solvent. The third material or the fourth material may include a nano-precursor, an anti-solvent, a quenching material, or a surfactant. Any other material that may be used to prepare nanoparticles may be included without limitation. In particular, since the present disclosure uses the tube fitting member to connect the tube to the first connector 110 or to the second connector, it is possible to use not only one type of nano-precursor but also other types of nano-precursors as the reactant, and it is the same with the anti-solvent. In addition, during the reaction, a material such as a quenching material or a surfactant may be injected.

The first material and the second material may be mixed while forming a turbulent flow in the first conduit.

A Reynolds number of the solution flow formed by mixing the first material and the second material may be 800 or more, more preferably 1000 or more, more preferably 1500 or more, more preferably 2000 or more, more preferably 3000 or more. In addition, it may be 5000 or less.

Figure 4:
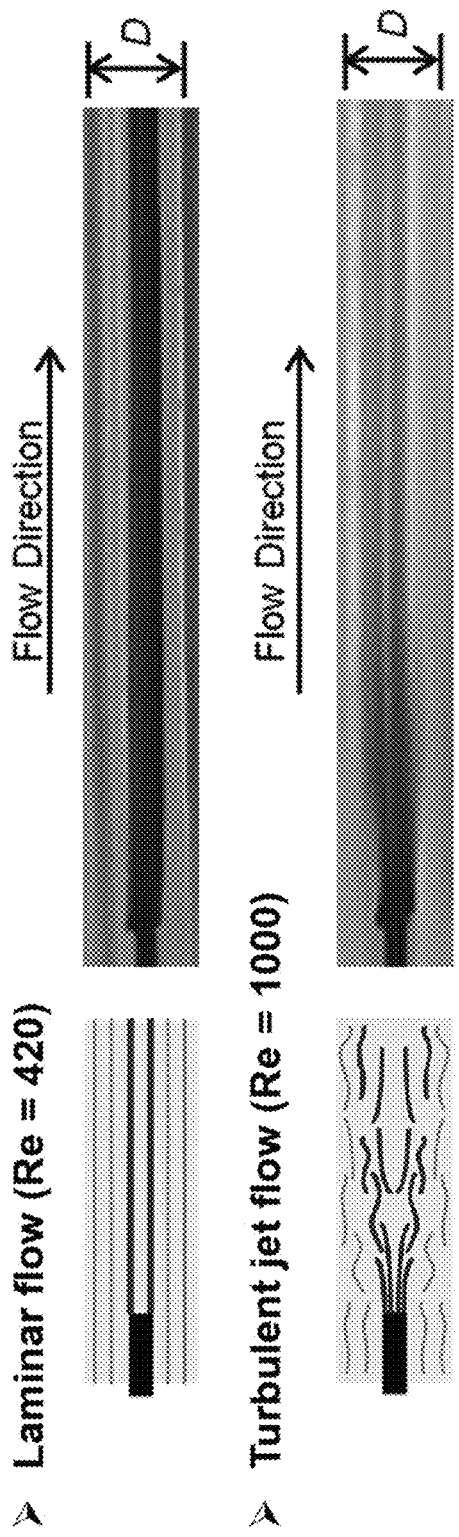
FIG. 4 illustrates comparison of fluid flow in a first conduit 130 in a device 100 for producing nanoparticles according to an embodiment of the present disclosure.

In an embodiment of the present disclosure, physicochemical properties such as particle size and uniformity of the nanoparticles may be controlled by adjusting the Reynolds number of the mixed solution flow in the first conduit 130 in the manufacturing of the nanoparticles. FIG. 4 illustrates the inside of the first conduit 130 according to the Reynolds number of the mixed solution flow in the first conduit 130. It is appreciated that when a value of the Reynolds number is adjusted to 420, laminar flow is formed within the first conduit 130, and when the value of the Reynolds number is adjusted to 1000, turbulence is formed within the first conduit 130. When laminar flow is formed, the time for mixing the reactants is long, and it is difficult to complete mixing. However, when turbulence is formed, mixing occurs within a short time, and mixing becomes easier.

Nanoparticles formed in the forming of the nanoparticles by mixing the first material and the second material in the first conduit 130 may be precipitated (nanoprecipitation) or may be formed in an emulsion state. In addition, as described above, nanoparticles having a uniformly distributed size may be formed. In addition, the size and uniformity of the formed nanoparticles may vary by controlling the Reynolds number of the mixed solution flow as described above.

The nanoparticles produced by the device 100 for preparing the nanoparticles may be at least one of: high molecular weight polymers including, for example, polystyrene, PLGA-PEG, gold, silver, silica, disulfide, iron oxide, siRNA/PEI, lipid vesicles, drug molecules, fluorescent molecules, reactive oxygen species (ROS)-reactive drug delivery nanoparticles.

A formation rate of the produced nanoparticles may be 10 mg/min or more, 20 mg/min or more, 30 mg/min or more, or 40 mg/min or more. Alternatively, it may be less than or equal to 1000 mg/min.

As an example, it is possible to prepare ROS-reactive drug delivery nanoparticles which is controlled in terms of their size, and significantly improved in terms of dispersion stability and sensitivity to reactive oxygen species (ROS) by using such a device for producing nanoparticles.

In addition, as an example, the reactive oxygen species (ROS)-reactive drug delivery nanoparticle may include a ferrocene functional group.

In addition, as an example, the reactive oxygen species (ROS)-reactive drug delivery nanoparticle may further include a carboxylic acid functional group.

In addition, as an example, the first material may be a reactive oxygen species (ROS)-reactive precursor solution or the second material may be a non-solvent.

A method for preparing reactive oxygen species (ROS)-reactive drug delivery nanoparticles using the device for producing nanoparticles according to an embodiment of the present disclosure includes: preparing a polymer including reactive oxygen species (ROS)-reactive functional groups; dissolving the prepared polymer including the reactive oxygen species (ROS)-reactive functional group in a solvent to prepare a reactive oxygen species (ROS)-reactive precursor solution; continuously supplying the prepared reactive oxygen species (ROS)-reactive precursor solution to the first conduit using the first supply and concurrently (e.g., simultaneously with the supplying of the ROS-reactive precursor solution) and continuously supplying a non-solvent to the first conduit using the second supply; mixing the reactive oxygen species (ROS)-reactive precursor solution supplied to the first conduit and the non-solvent supplied to the second conduit in the first conduit; and forming reactive oxygen species (ROS)-reactive drug delivery nanoparticles from the mixed material in the first conduit.

In an embodiment, a concentration of the reactive oxygen species (ROS)-reactive precursor solution prepared in the preparing of the reactive oxygen species (ROS)-reactive precursor solution may be 3 to 15 mg/mL, 5 to 13 mg/mL, or 8 to 11 mg/mL.

In an embodiment, in the continuously supplying to the first conduit, the method may further include concurrently and continuously supplying a non-solvent to the first conduit using the third supply.

In addition, the mixing in the first conduit may include mixing while forming turbulence.

In addition, in the mixing in the first conduit, a Reynolds number of the mixed solution flow in the first conduit may be 1000 to 4000, 1000 to 3000, or 1500 to 2500.

In addition, a production rate of the reactive oxygen species (ROS)-reactive drug delivery nanoparticles may be 500 to 1000 mg/min.

In addition, the method may further include, after forming of the reactive oxygen species (ROS)-reactive drug delivery nanoparticles, lyophilizing (e.g., freeze-drying) without a cryoprotectant.

I. Preparation of Polystyrene Nanoparticles

Embodiment 1 and Experimental Example 1

A device 100 for producing nanoparticles according to an embodiment of the present disclosure was manufactured. Polystyrene (MW: 350,000) was dissolved in tetrahydrofuran (THF) at a concentration of 1 mg/ml, and then flowed into a conduit through a single tube using a diaphragm pump. Then, water was injected to flow in the conduit through two tubes. A Reynolds number was calculated using a total flow rate corresponding to a sum of two flow rates, and the results of calculating a production rate of nanoparticles accordingly is shown in Table 1 below.

TABLE 1

| Reynolds number | 1000 | 2000 | 3000 |
|---|---|---|---|
| Total flow rate | 121 mL/min | 242 mL/min | 363 mL/min |
| Production rate of PS NPs (1 mg/mL) | 11 mg/min | 22 mg/min | 33 mg/min |

According to the experimental results, it was appreciated that as the flow rate according to the Reynolds number increased, the production rate of the formed polystyrene nanoparticles also increased by the same multiple.

Figure 5:
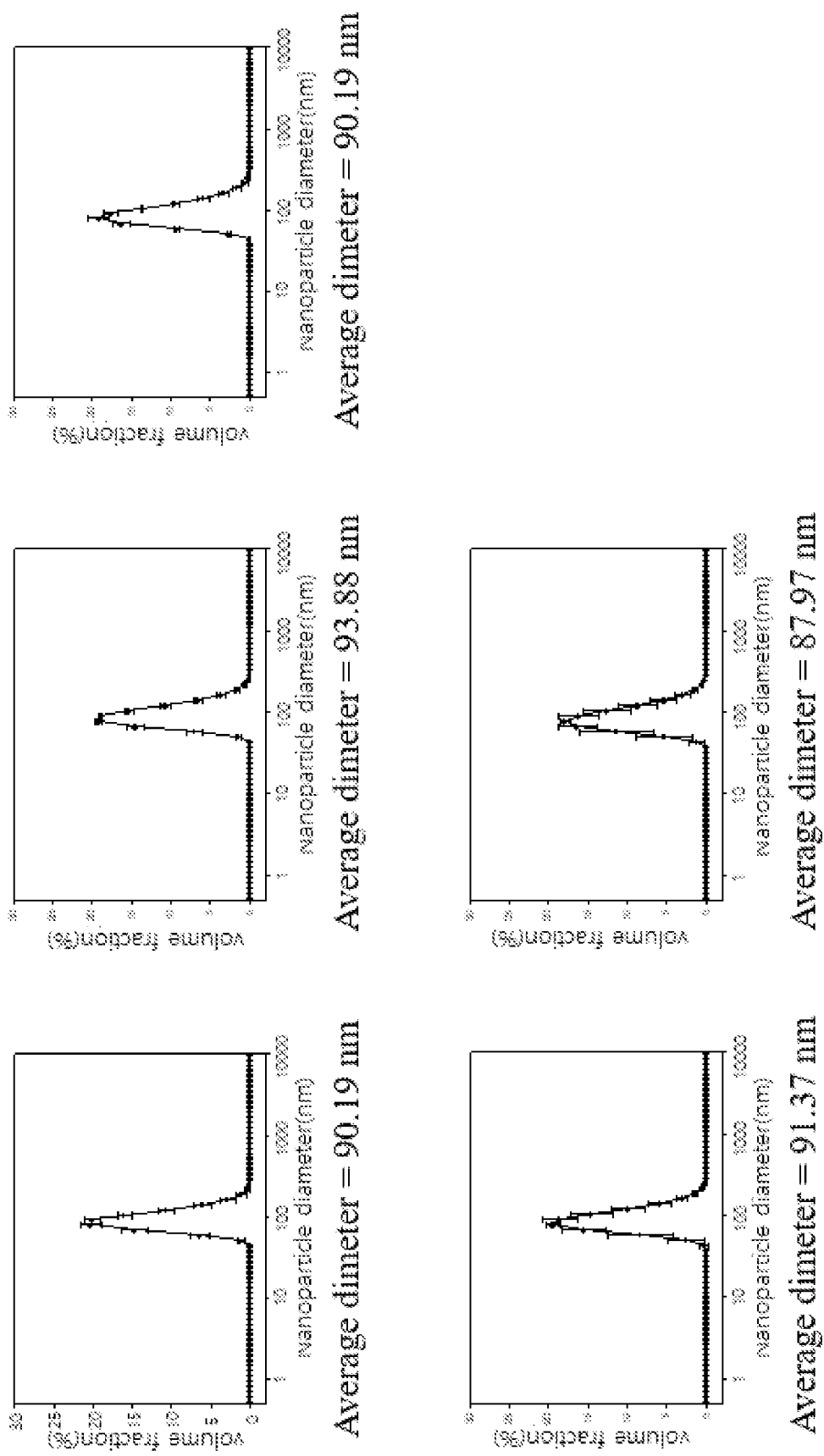
FIG. 5 is a graph showing a volume fraction according to diameters of polystyrene nanoparticles produced using the device 100 for producing nanoparticles according to an embodiment of the present disclosure.

In addition, a graph showing a volume fraction according to the diameter of the polystyrene nanoparticles formed when the Reynolds number is 3000 in Embodiment 1 is shown in FIG. 5. Polystyrene (MW: 350,000) was dissolved in tetrahydrofuran (THF) at a concentration of 1 mg/ml, and then flowed in a conduit through a single tube at a flow rate of 33 mL/min using a diaphragm pump. Next, water was injected to flow in the conduit through two tubes at a flow rate of 330 mL/min. The Reynolds number of the total flow rate was 3000.

Accordingly, when polystyrene nanoparticles were prepared several times under the same conditions, it was appreciated that average size and size distribution of the nanoparticles were significantly similar. In other words, it was appreciated that polystyrene nanoparticles with good homogeneity were continuously produced at each production.

Embodiment 2

A device 100 for producing nanoparticles according to an embodiment of the present disclosure was manufactured. Polystyrene (MW: 350,000) was dissolved in tetrahydrofuran (THF) at a concentration of 1 mg/ml, and then flowed into a conduit through a single tube using a diaphragm pump at a flow rate of 27.5 mL/min. Then, water was injected to flow in the conduit through two tubes at a flow rate of 275 mL/min. The Reynolds number of the total flow rate was 2500.

Comparative Examples 1 and 2

First, a hole was defined at a flat portion of a T-shaped connector made of polytetrafluoroethylene by using a drill, a needle (e.g., syringe) was then inserted thereto and fixed with an optical adhesive, and thus a device 100 for producing nanoparticles was manufactured. Next, a syringe pump was used to flow the same polystyrene precursor solution as in Embodiment 2 through a conduit through the syringe. Next, the syringe pump was used to allow water to flow through the conduit. The Reynolds number of the total flow rate was the same as in Embodiment 2. The particles prepared as in the above are to be defined as Comparative Example 1.

Polystyrene microspheres synthesized by emulsion polymerization available at Bangs labs were used as Comparative Example 2. The fine particles were obtained by adding a crosslinking agent (Divinylbenzene, etc.) and an initiator to a polystyrene monomer, followed by reacting at 70 to 90° C. for 6 to 20 hours in a batch reactor.

Experimental Example 2

Figure 6:
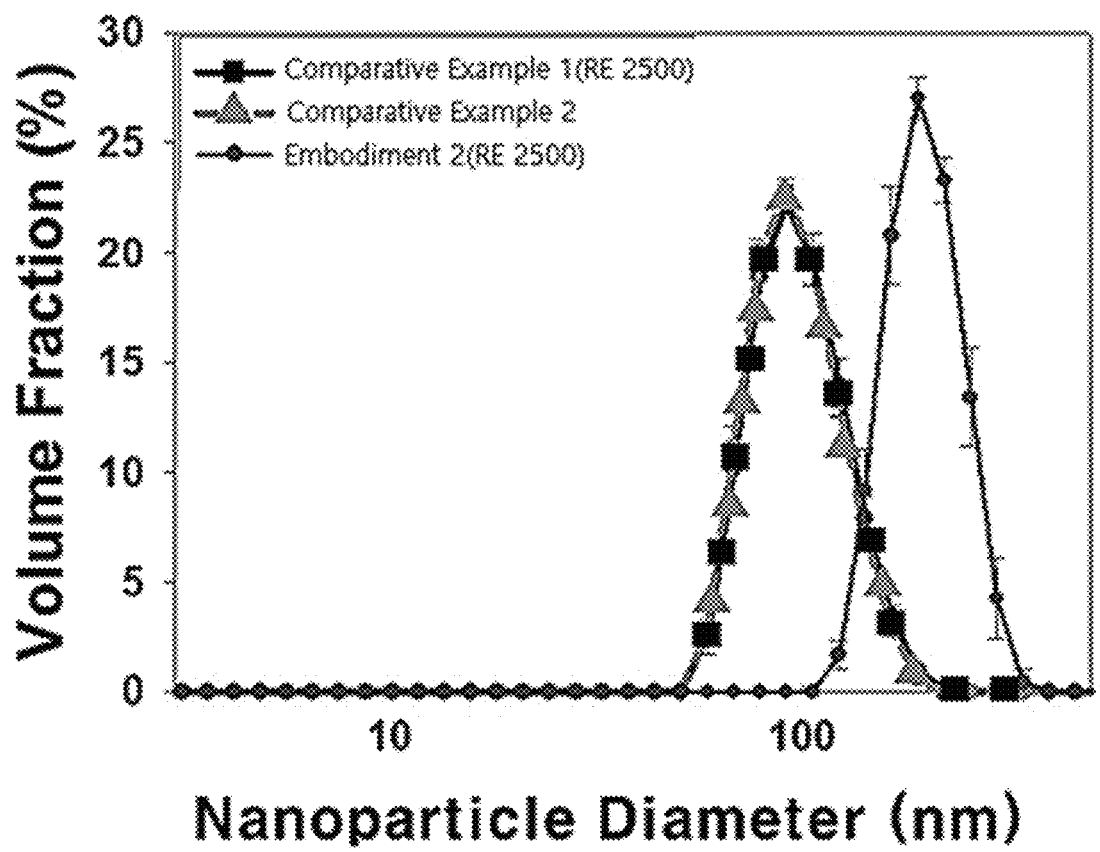
FIG. 6 is a graph comparing a volume fraction according to diameters of polystyrene nanoparticles produced using the device 100 for producing nanoparticles according to an embodiment of the present disclosure to that of Comparative Example.

For each of Embodiment 2, Comparative Example 1 and Comparative Example 2, a graph showing the volume fraction according to the diameter of the particles is shown in FIG. 6. Accordingly, it was appreciated that the nanoparticles prepared in Embodiment 2 have more uniform size distribution than the nanoparticles of Comparative Examples 1 and 2.

Embodiment 3

A device 100 for producing nanoparticles according to an embodiment of the present disclosure was prepared. Polystyrene (MW: 350,000) was dissolved in tetrahydrofuran (THF) at a concentration of 1 mg/ml, and then flowed into a conduit through a single tube using a diaphragm pump at a flow rate of 33 mL/min. Then, water was injected to flow in the conduit through two tubes at a flow rate of 330 mL/min. The Reynolds number of the total flow rate was 3000.

Experimental Example 3

Figure 7:
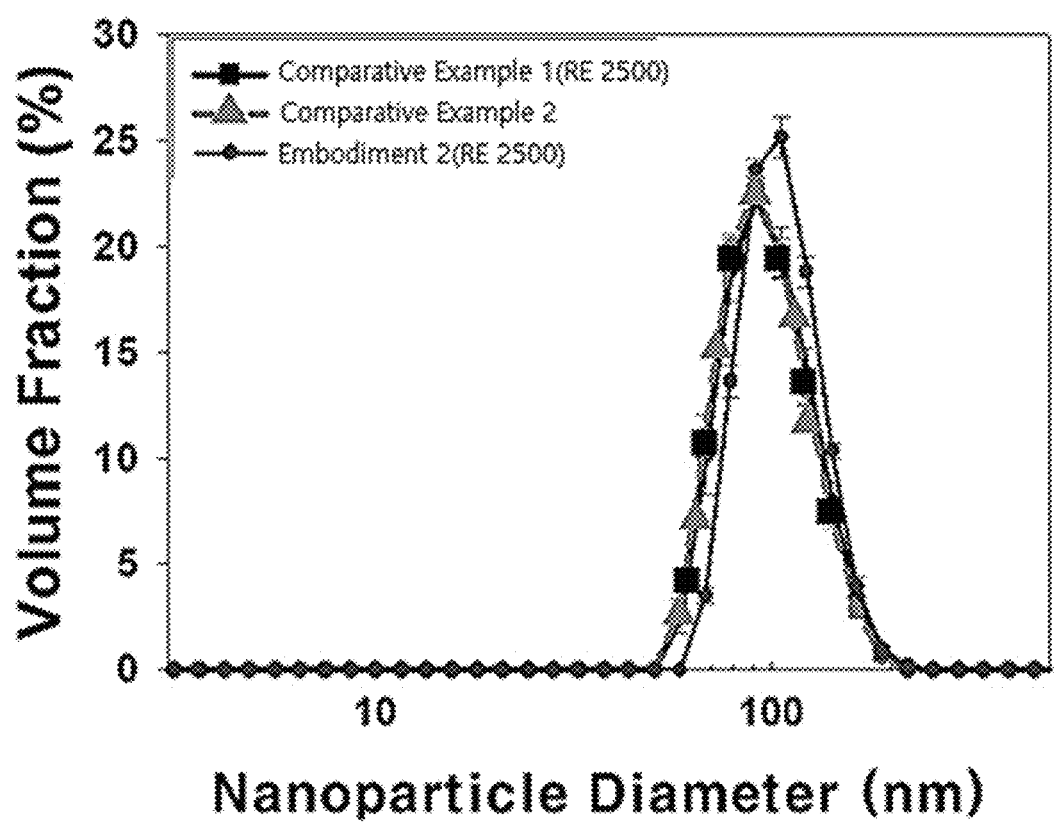
FIG. 7 is a graph comparing a volume fraction according to diameters of polystyrene nanoparticles produced using the device 100 for producing nanoparticles according to an embodiment of the present disclosure to that of Comparative Example.
Figure 8:
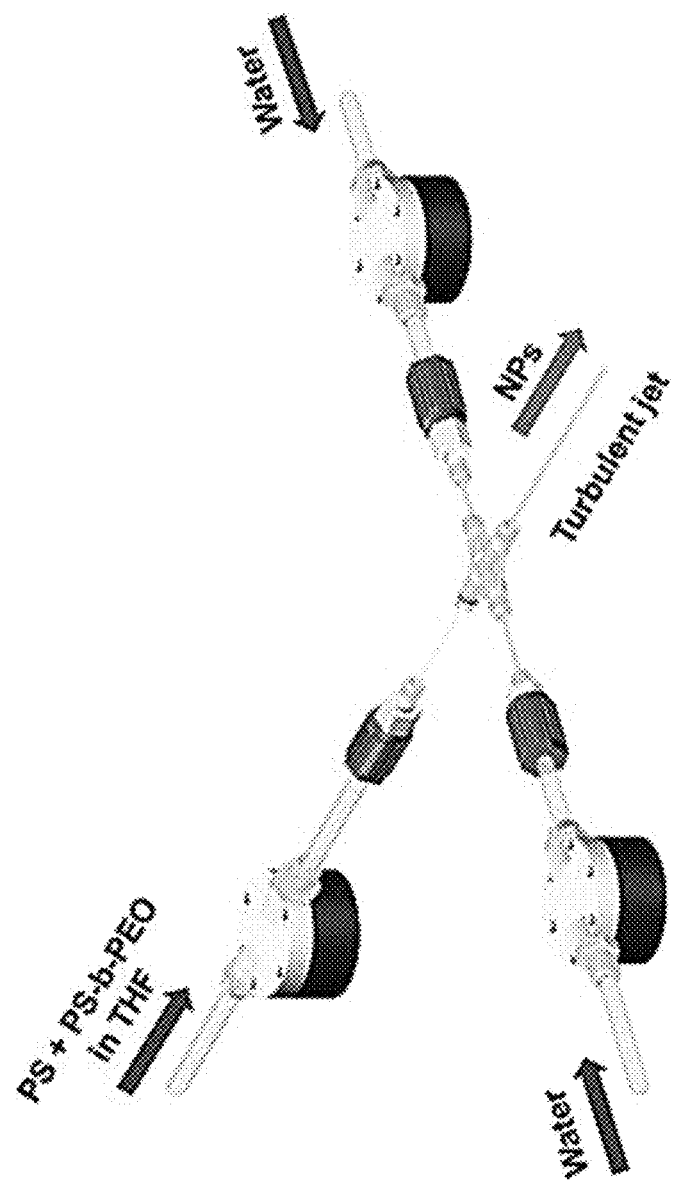
FIG. 8 illustrates an example of implementing a device for producing nanoparticles according to an embodiment.

For each of Embodiment 3, Comparative Example 1 and Comparative Example 2, a graph showing the volume fraction according to the diameter of the particles is shown in FIG. 7.

Accordingly, it was appreciated that the nanoparticles prepared in Embodiment 3 have more uniform size distribution than the nanoparticles of Comparative Examples 1 and 2.

In addition, it was appreciated that nanoparticles having a smaller average diameter may be prepared by increasing the Reynolds number of the total flow rate by increasing the flow rate, as compared to Embodiment 2.

I. Preparation of Polystyrene Nanoparticles

Comparative Example II

Preparation of Polystyrene Nanoparticles (PS NP) by Bulk Synthesis

In order to improve dispersion stability of nanoparticles in centrifugation and redistribution processes of a polymer suspension, a PS-b-PEO (Polystyrene-Poly(ethylene oxide)) block copolymer was added to a polystyrene (PS) precursor solution.

In order to optimize a weight ratio of PS to PS-b-PEO, the nanoparticle size distribution was analyzed before centrifugation and after four times of centrifugation and redistribution, while increasing the weight ratio of PS-b-PEO in the polymer.

Figure 9:
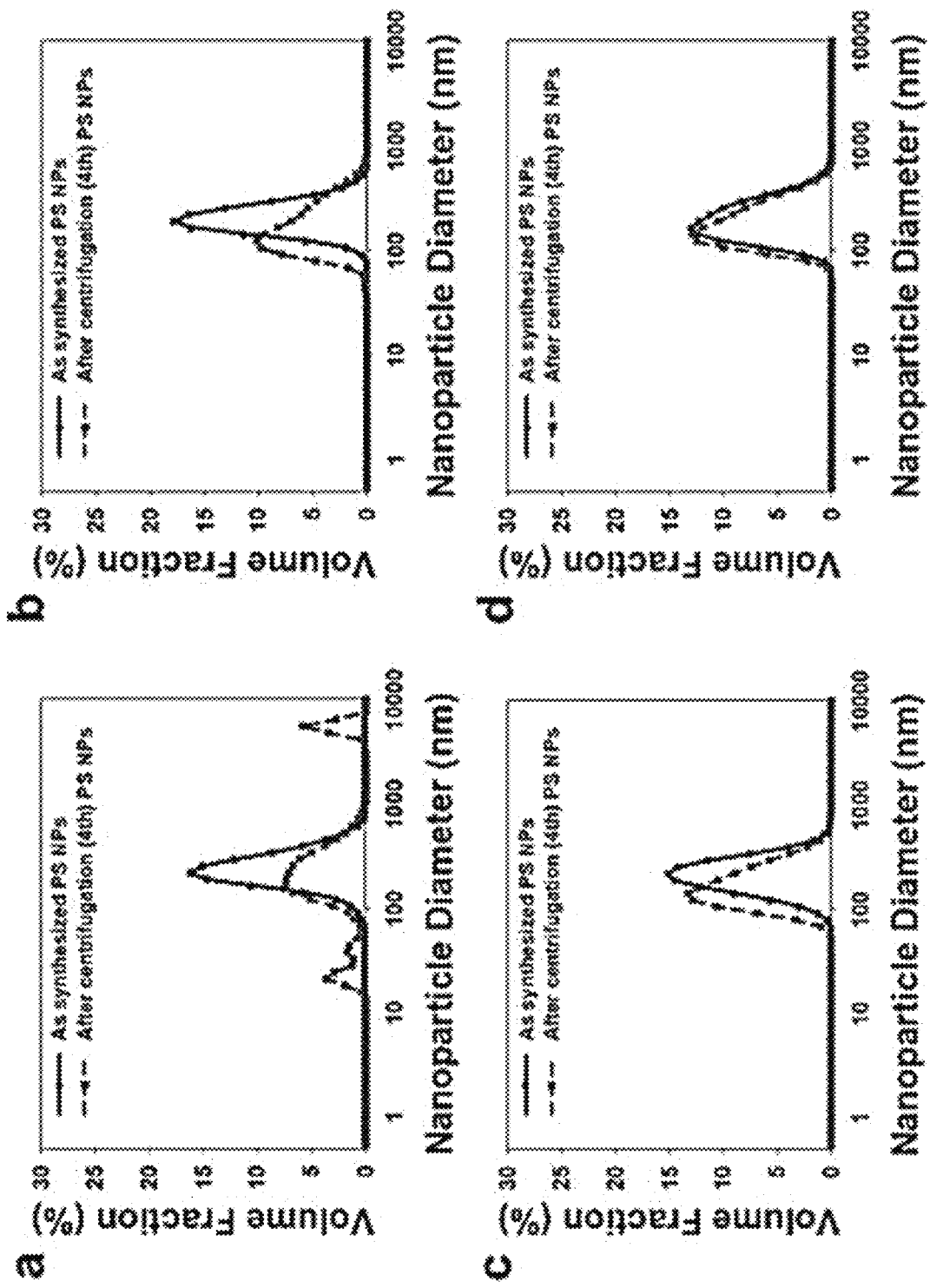
FIG. 9 illustrates size distribution of polystyrene nanoparticles according to a weight ratio of PS to PS-b-PE0 of (a) 0 wt %, (b) 12.5 wt %, (c) 25 wt %, and (d) 37.5 wt % in a bulk synthesis method according to an embodiment.

Referring to FIG. 9, it was appreciated that the PS NP particles synthesized in an aqueous medium have uniform size distribution and similar average size, regardless of the addition of PS-b-PEO before the centrifugation process. However, in the case (a) of PS NP without PS-b-PEO added to the aqueous medium, it was polydispersed after four times of centrifugation and redistribution. When the weight ratio of PS-b-PEO was (b) 12.5 wt % and (c) 25 wt %, after four times of centrifugation and redispersion, the nanoparticle size distribution was further improved, but finely became non-Gaussian, as compared to the case where PS-b-PEO was not added. In addition, the average size of NP decreased after four times of centrifugation and redispersion. Since the content of PS-b-PEO was small, steric hindrance was insufficient to improve dispersion stability against centrifugation. When the weight ratio of PS-b-PEO was (d) 37.5 wt %, the size distribution of NP was uniform after four times of centrifugation and redistribution. In addition, the average size of NP did not significantly change.

It was appreciated that problems of dispersion stability in the centrifugation and redistribution process may be solved by steric hindrance through the addition of PS-b-PEO and optimization of the content. However, in the bulk synthesis method, when PS-b-PEO was added at a concentration of 25% by weight or more, the NP size distribution was widened both before and after centrifugation and redistribution processes.

Embodiment II

Preparation of PS Nanoparticles Using the Device for Producing Nanoparticles

Figure 10:
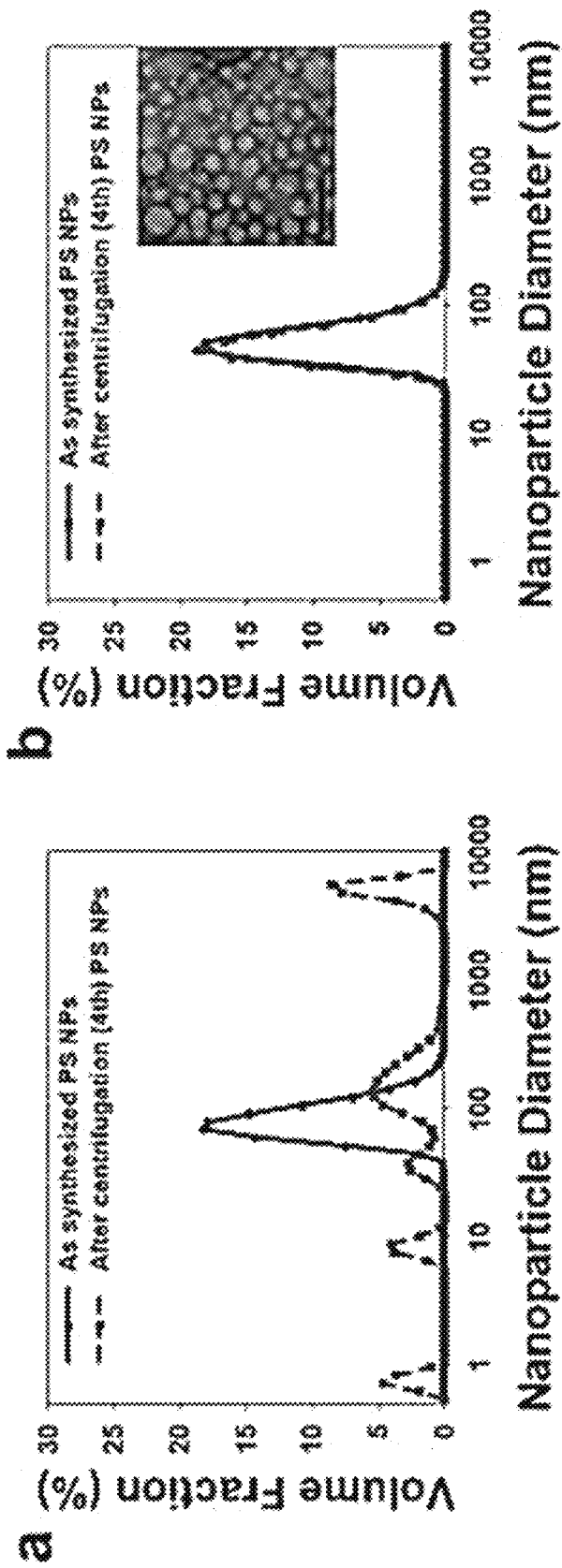
FIG. 10 illustrates size distribution and TEM image of polystyrene nanoparticles according to a weight ratio of PS to PS-b-PE0 of (a) 0 wt % and (b) 37.5 wt % in a method of producing nanoparticles using the device for producing nanoparticles according to an embodiment.

Referring to a of FIG. 10, when using the device for producing nanoparticles according to an embodiment of the present disclosure, the average NP size was smaller and the NP size distribution was narrower, regardless of the addition of PS-b-PEO. Although PS-b-PEO was not added, the size distribution of PS NP did not significantly change over several weeks in an aqueous medium.

In order to improve dispersion stability by steric hindrance, nanoparticles containing 37.5 wt % of PS-b-PEO were prepared. The dispersion stability of PS NP was most improved in the weight ratio. Referring to b of FIG. 10, when using the device for producing nanoparticles according to an embodiment of the present disclosure, it was appreciated that dispersion stability in an aqueous medium was improved even after repeating four times of centrifugation and redistribution, and in particular, the average size was smaller and the size distribution was narrow as compared to that of the NP prepared in the bulk synthesis method.

Accordingly, it was appreciated that the dispersion stability of the nanoparticles is maintained even after repeating four times of centrifugation and redistribution by introducing the polystyrene-polyethylene oxide block copolymer and optimizing the weight ratio.

I. Preparation of Nanoparticles Containing Ferrocene

<Synthesis of Ferrocene Polymer by Radical Polymerization Reaction>

After dissolving 2 mmol of ferrocenylmethyl methacrylate (FMMA), 10 mmol of methacrylic acid (MA, 99%) and 0.12 mmol of AIBN, a radical initiator, in 10 ml of anhydrous tetrahydrofuran (THF), polymerization reaction was carried out by stirring at 70° C. for 24 hours. A purity of the ferrocene polymer was measured by 1H NMR. A molecular weight (Mw) and a polydispersity index (PDI) of the polymer were analyzed by gel permeation chromatography (GPC) using THF as an eluent at a flow rate of 1.0 mL/min at 35° C.

Embodiment III-1

Preparation of Ferrocene Nanoparticles (D-FNP) Using the Device for Producing Nanoparticles A ferrocene precursor solution was prepared by dissolving the ferrocene polymer prepared by the radical polymerization reaction in THE.

Embodiment 1 (D-FNP1) is a case where a concentration of the ferrocene precursor solution is 5 mg/mL, and Embodiment 2 (D-FNP2) is a case where the concentration is 10 mg/mL.

Figure 11:
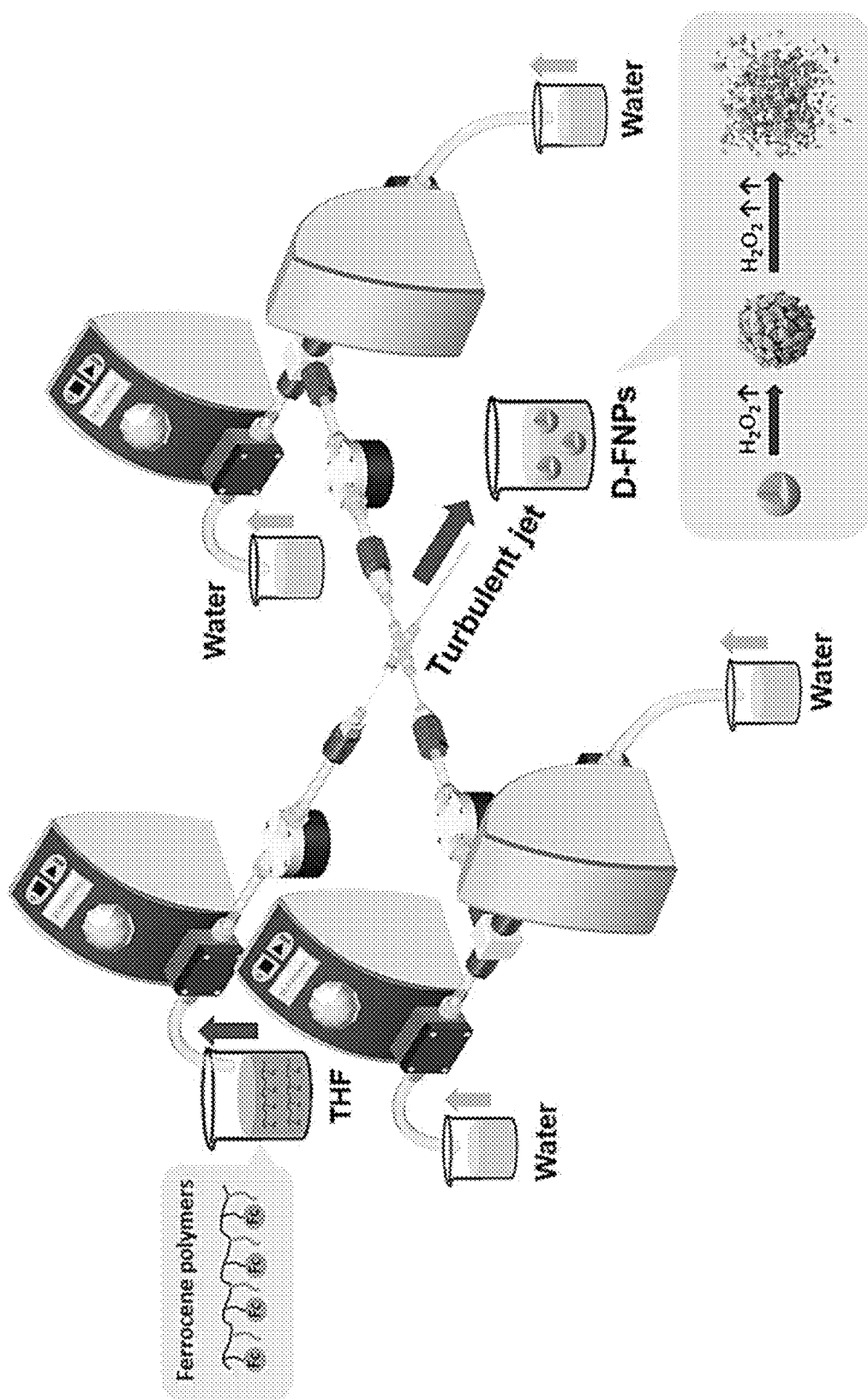
FIG. 11 illustrates a photograph illustrating a process of preparing ferrocene nanoparticles using a device for producing nanoparticles according to an embodiment.

Next, ferrocene nanoparticles (D-FNP1, 2) were produced using the device for producing nanoparticles according to the above embodiment (FIG. 11).

FIG. 11 shows a case where the ferrocene precursor solution and water or deionized water are respectively added. An average Reynolds number was calculated by Formula Re=QD/vA, where Q, v, D and A mean the total flow rate of the fluid mixture, kinematic viscosity, outer tube diameter and cross-sectional area, respectively. To calculate the Re value, the kinematic viscosity v of the water-THF mixture was calculated by values of μ and ρ which are already reported in the water-THF mixture. Re was adjusted to 2,000, and a ratio of the volume flow rate of an inner flow to an outer flow was adjusted to 1:5. The nanoparticle suspension was placed in a vacuum oven at a vacuum gauge of −0.08 MPa at 25° C. for 2 hours to remove residual organic solvent.

Comparative Example III-1

Preparation of Ferrocene Nanoparticles (B-FNP) by Bulk Synthesis

A ferrocene precursor solution was prepared by dissolving the ferrocene polymer prepared by the radical polymerization reaction in THF.

1 mL of the precursor solution was added dropwise to 5 mL of deionized water and stirred in a stirrer for 5 minutes to prepare ferrocene nanoparticles (B-FNP).

Experimental Example III-1

Figure 12A:
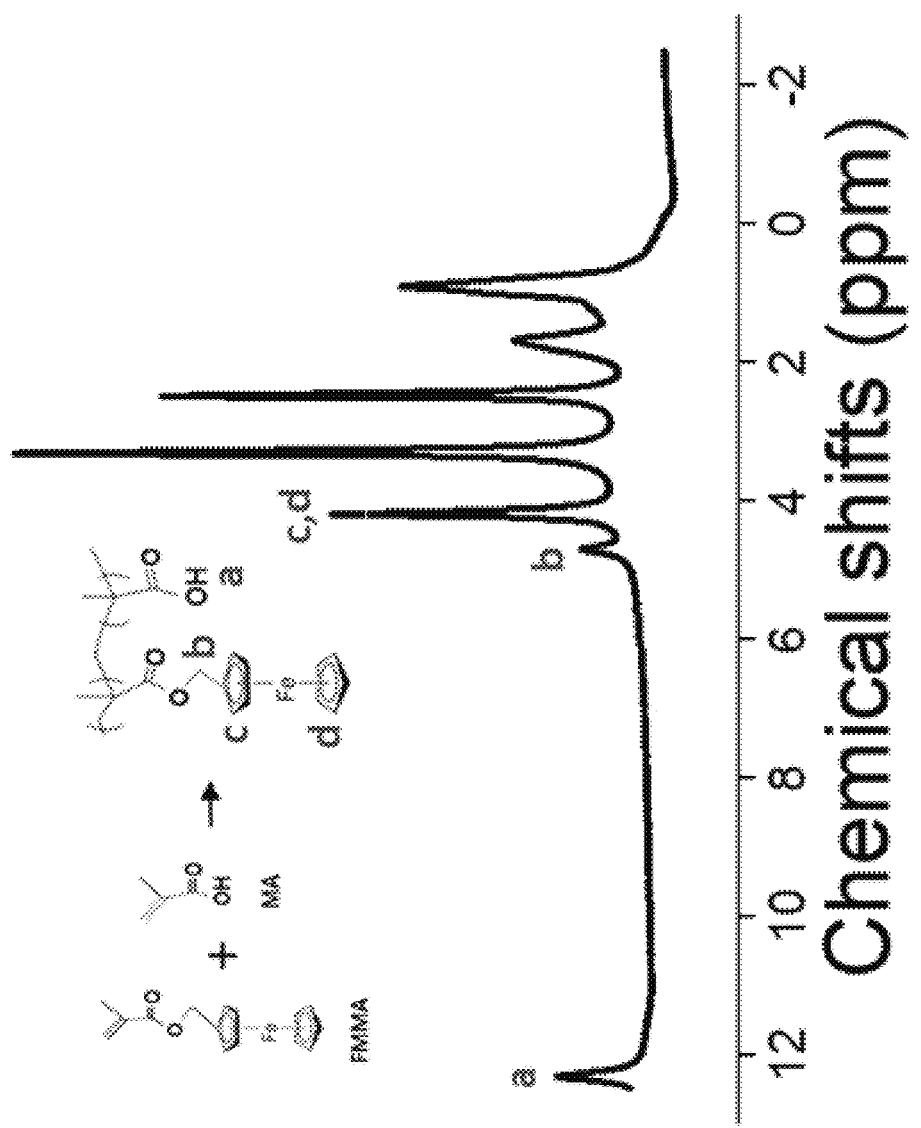
FIGS. 12(a) and 12(b) illustrate analysis results of (a) 1H-NMR and (b) GPC of a ferrocene polymer according to an embodiment.

Analysis Results on Characteristics of Ferrocene Polymer and Ferrocene Nanoparticles The ferrocene polymer synthesized by the radical polymerization reaction is composed of FMMA having a hydrophobic ferrocene part (e.g., moiety) and MA having a hydrophilic COOH group. The results of 1H NMR analysis of the ferrocene polymer is shown in FIG. 12(a). It was analyzed as δ=12.4 (br, 1H, COOH of MA), 4.8 (br, 2H, CO2-CH2 of FMMA), 4.2 (br, 9H of FMMA), (3.7-3.3) (br, 20H), (2.7-2.5) (br, 18H), (2.0-1.7) (br, 15H), and (1.1-0.8) (br, 17H) ppm.

Typical monomer peaks for methacrylate protons appear at 5.56 and 6.08 ppm, and the peaks are generally sharp. After polymerization, the monomer peaks disappeared completely, and a broad alkyl chain peak of the polymer was clearly identified at 0.8-2.0 ppm. This means that the ferrocene polymer has been successfully synthesized. Interestingly, new peaks were identified at 12.4, 4.8 and 4.2 ppm, due to protons of ferrocene and carboxyl groups of the ferrocene polymer.

Figure 12B:
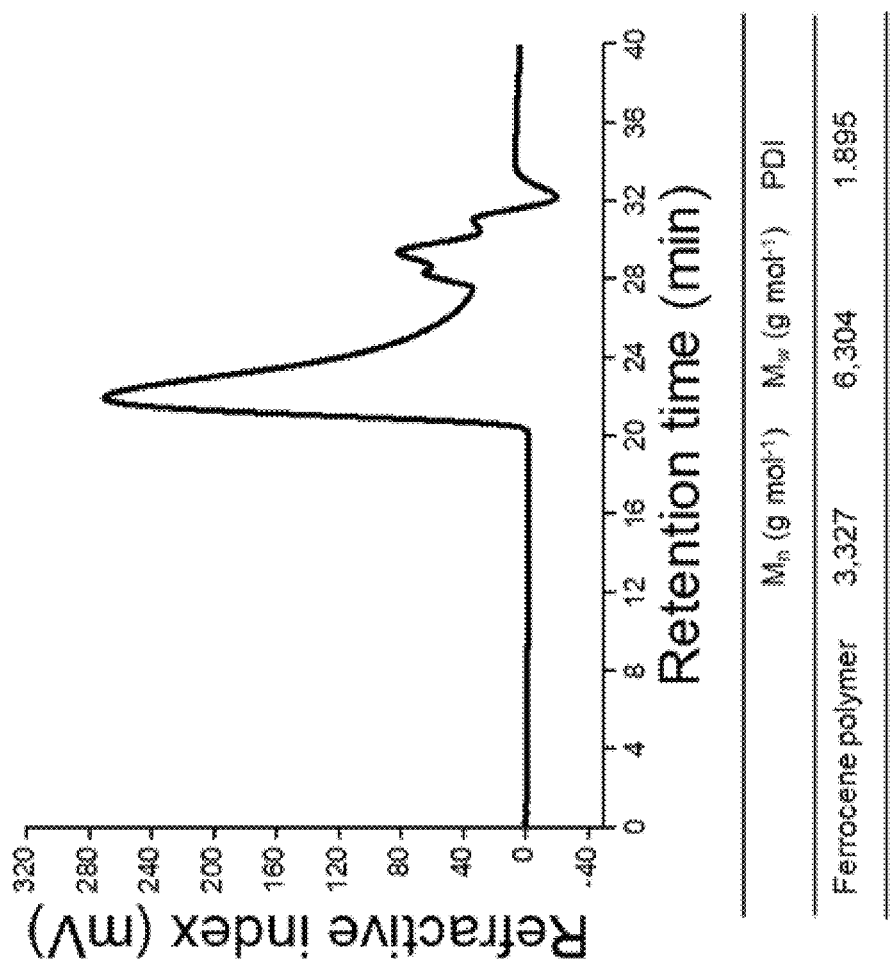

According to the GPC analysis results of the ferrocene polymer in FIG. 12(b), a molecular weight (Mw) and a polydispersity index (PDI) were Mw=6,304 and Mw/Mn=1.895, and a polymer yield was 99%.

When Re was adjusted to 2,000, the ferrocene polymer precursor solution was rapidly mixed with the non-solvent deionized water by turbulent flow, and thus the hydrophobic ferrocene polymer was self-assembled into stable ferrocene nanoparticles.

Figure 13A:
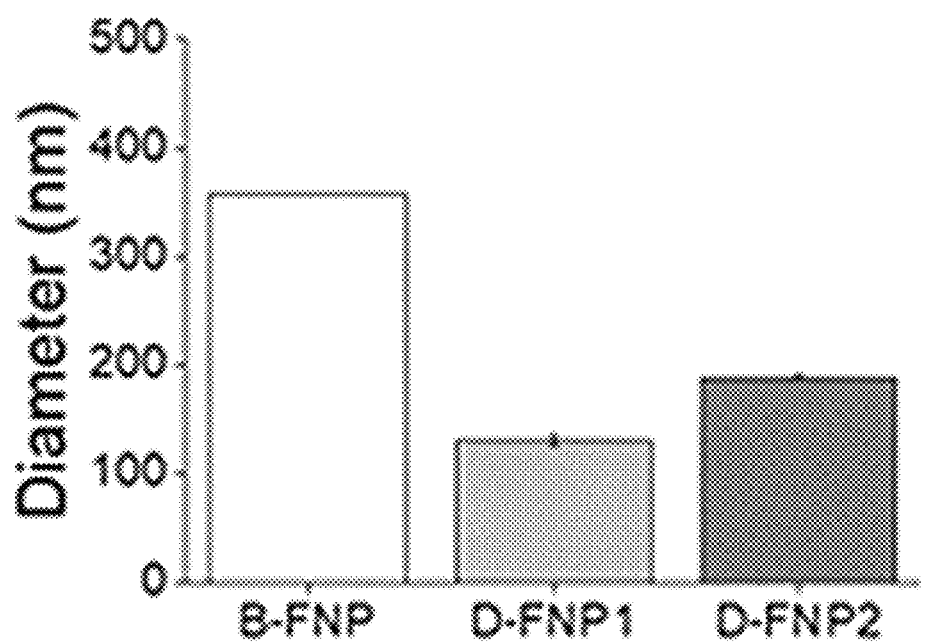
FIGS. 13(a)-13(d) illustrate analysis results of (a) hydrodynamic diameter, (b) polydispersity index (PDI), and (c) surface charge of ferrocene nanoparticles according to an embodiment, along with TEM analysis results of (d) D-FNP1 and (e) D-FNP2.
Figure 13B:
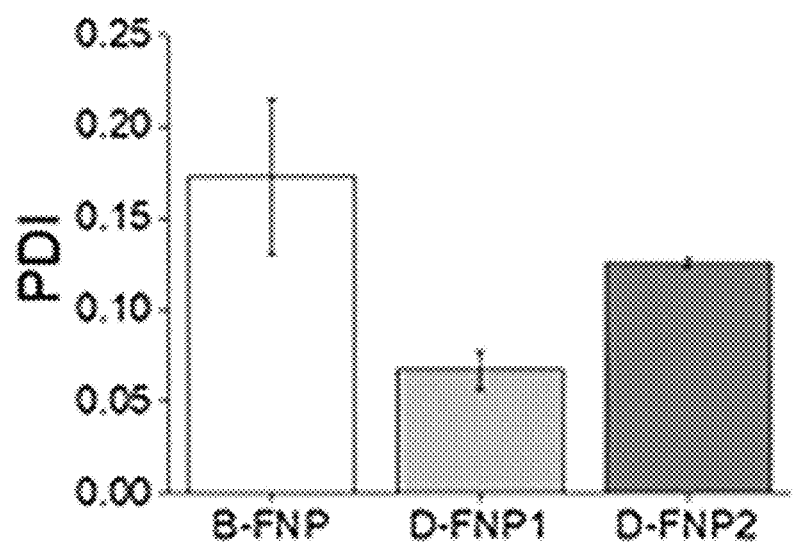
Figure 13C:
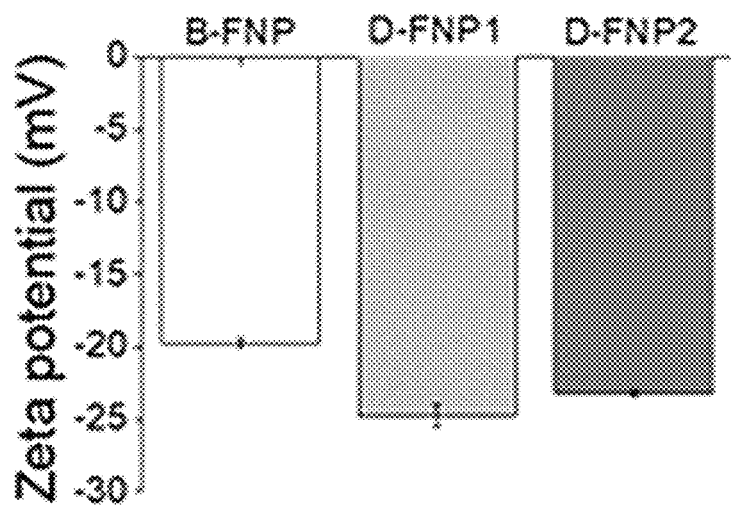
Figure 13D:
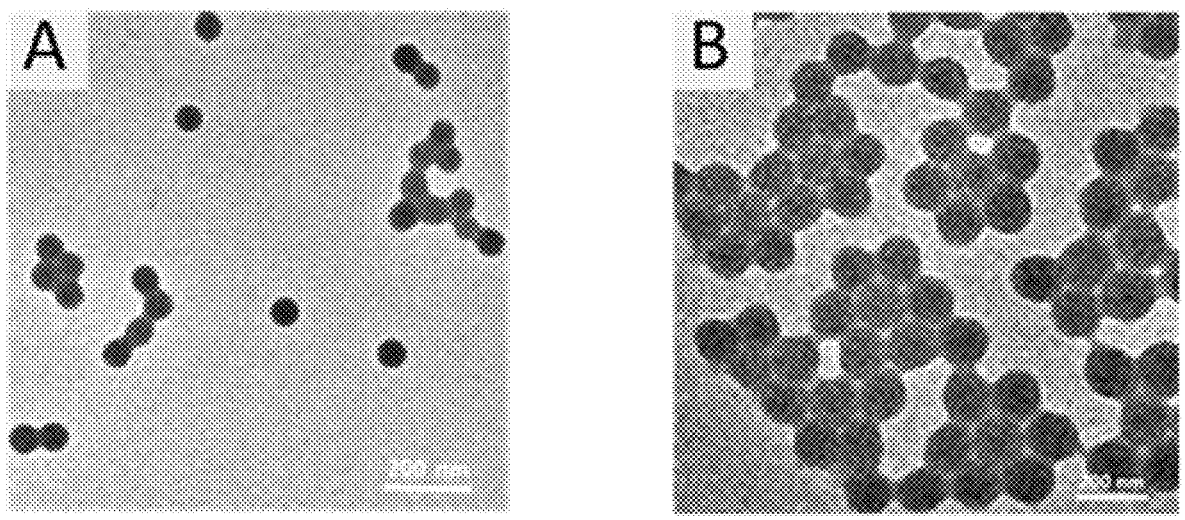

Referring to FIGS. 13(a)-13(c), it was appreciated that as compared to B-FNP, D-FNP had a smaller average diameter and lower PDI. In addition, it was appreciated that a zeta potential of D-FNP was smaller because a surface area per unit volume increases as an average size of the nanoparticles decreases. In the case of Comparative Example, it takes a long time to prepare the ferrocene nanoparticles, it is difficult to produce a uniform size distribution, and it is highly dependent on specific synthesis conditions. In the case of scaling-up for mass-production of nanoparticles, it was appreciated that the average diameter of the produced nanoparticles is larger, the PDI is higher, and partial aggregation occurs. On the other hand, referring to FIGS. 13(d)-(e), it was appreciated that the D-FNP has a small average size and uniform size distribution. This means that D-FNP was synthesized in a completely continuous manner by the producing method using the device for producing nanoparticles according to an embodiment.

As a result, mass production of D-FNP was easily achieved by simply pouring more precursor solution and non-solvent into each reservoir. According to an implementation, it was appreciated that when a 10 mg/mL of precursor solution was used and Re was fixed at 2,000, the production rate of D-FNP was 633 mg/min, that is, 332.7 kg/yr.

Analysis Results of Dispersion Stability of Ferrocene Nanoparticles

Using DLS, the dispersion stability was evaluated under the following two different conditions.

Figure 14A:
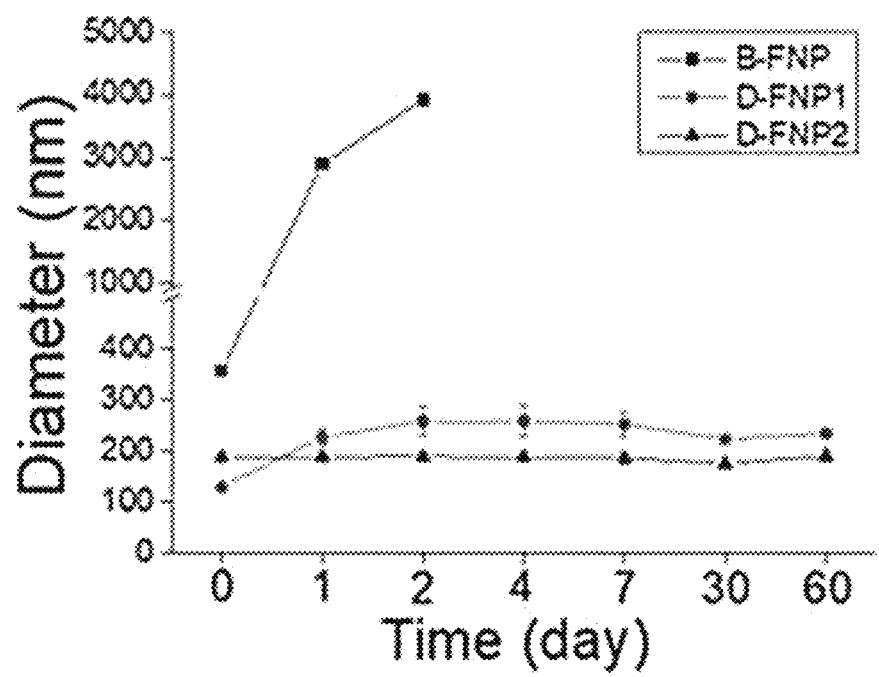
FIGS. 14(a)-14(d) illustrate analysis results of (a) hydrodynamic diameter and (b) polydispersity index (PDI) regarding long-term stability of ferrocene nanoparticles according to an embodiment, along with (c) analysis results of hydrodynamic diameter and (d) surface charge regarding stability after lyophilization followed by re-dispersion.
Figure 14B:
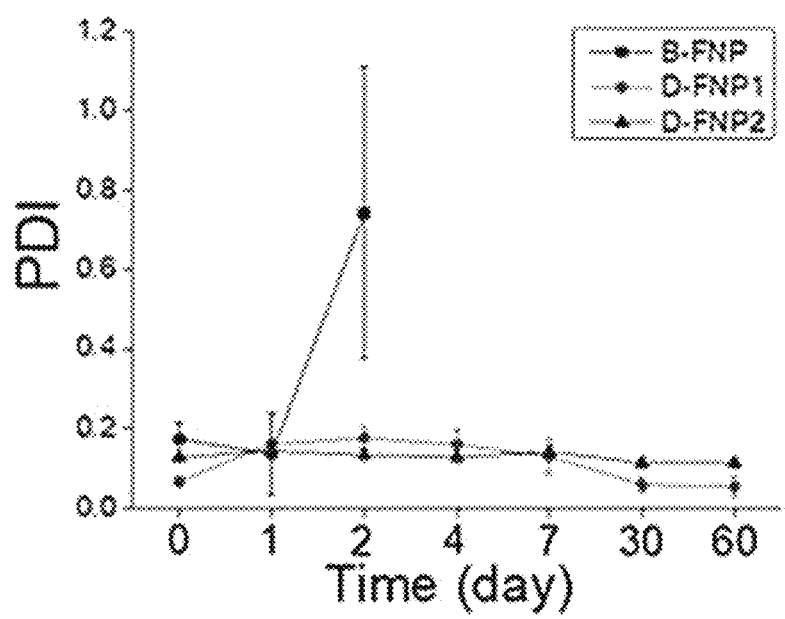

As a first condition, hydrodynamic diameters and PDI of B-FNP and D-FNP were analyzed for 2 months in an aqueous medium at room temperature, and the results are shown in FIG. 14(a)(b). B-FNP prepared by 5 mg/mL of the precursor solution was aggregated immediately after 1 day, and the diameter increased significantly. This means that B-FNP is greatly limited in stability over time. On the other hand, in the case of D-FNP1 prepared using 5 mg/mL of the precursor solution, the hydrodynamic diameter and PDI did not significantly change for 2 months. When the concentration of the precursor solution increases, the production rate of nanoparticles increases, but it is difficult to maintain the nanoparticle dispersion stability. However, even in the case of D-FNP2 using 10 mg/mL of the precursor solution, the hydrodynamic diameter and PDI did not substantially change for 2 months, and stable dispersion stability in an aqueous medium for 2 months was identified.

Figure 14C:
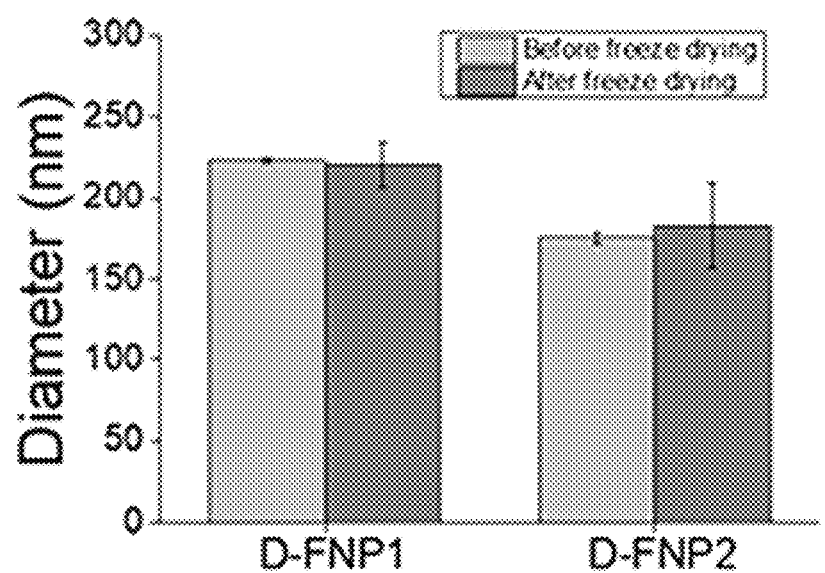
Figure 14D:
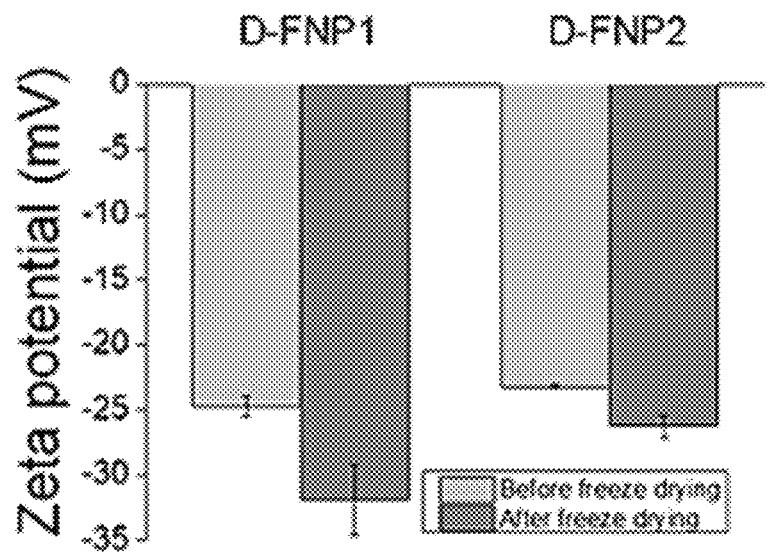

As a second condition, D-FNP was lyophilized and redispersed in a biological buffer (PBS, pH 7.4), and the results are shown in FIG. 14(c)(d). In an embodiment, although it was prepared without a cryoprotectant such as sucrose, trehalose, or glucose, it was appreciated that it was easily redispersed without significant change. In the case of B-FNP, since partial aggregation was observed at the beginning of manufacture, redispersing was not performed after lyophilizing. These results mean that D-FNP may provide a variety of platforms for drug delivery.

Analysis on Sensitivity of Reactive Oxygen Species (ROS) of Ferrocene Nanoparticles In order to evaluate the ROS sensitivity of D-FNP2, the effects of 100 mM of $H_2O_2$, a water-soluble oxidizing agent, on the size, surface charge, and shape were analyzed. After exposure to $H_2O_2$, a diameter of D-FNP2 increased significantly, and its effect was time dependent. This means that functional materials (drugs, etc.) contained in the ferrocene nanoparticles according to an embodiment may be selectively released to the external environment.

Figure 15A:
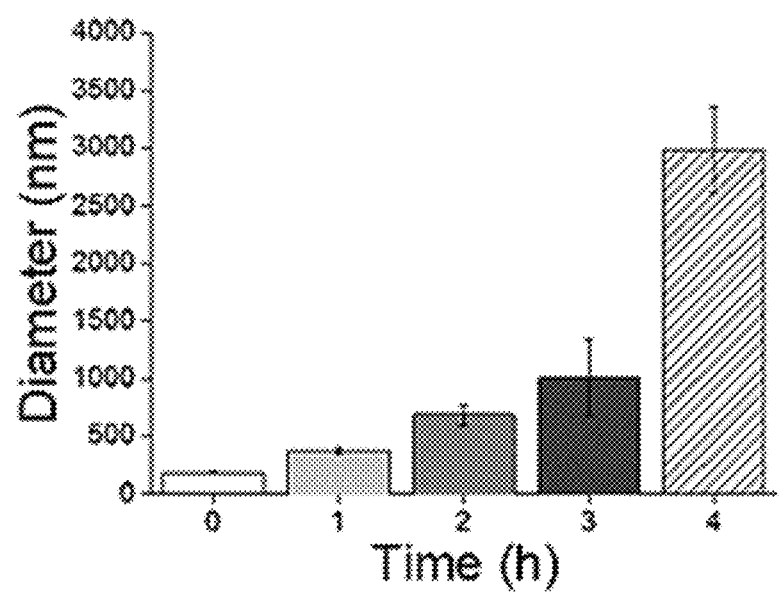
FIGS. 15(a)-15(c) illustrate analysis results of (a) hydrodynamic diameter and (b) surface charge regarding reactive oxygen species (ROS) sensitivity of ferrocene nanoparticles according to an embodiment, along with (c) TEM analysis results and of D-FNP2 before and after oxidation through $H_2O_2$ treatment.
Figure 15B:
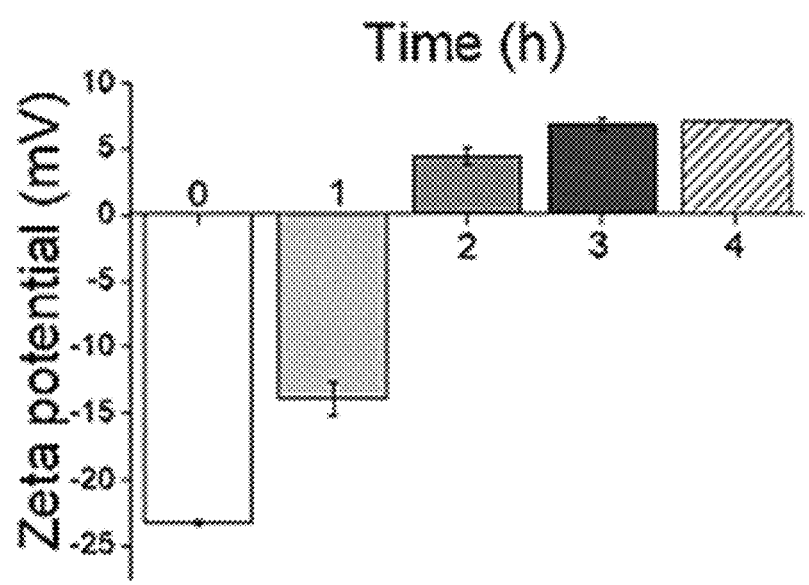
Figure 15C:
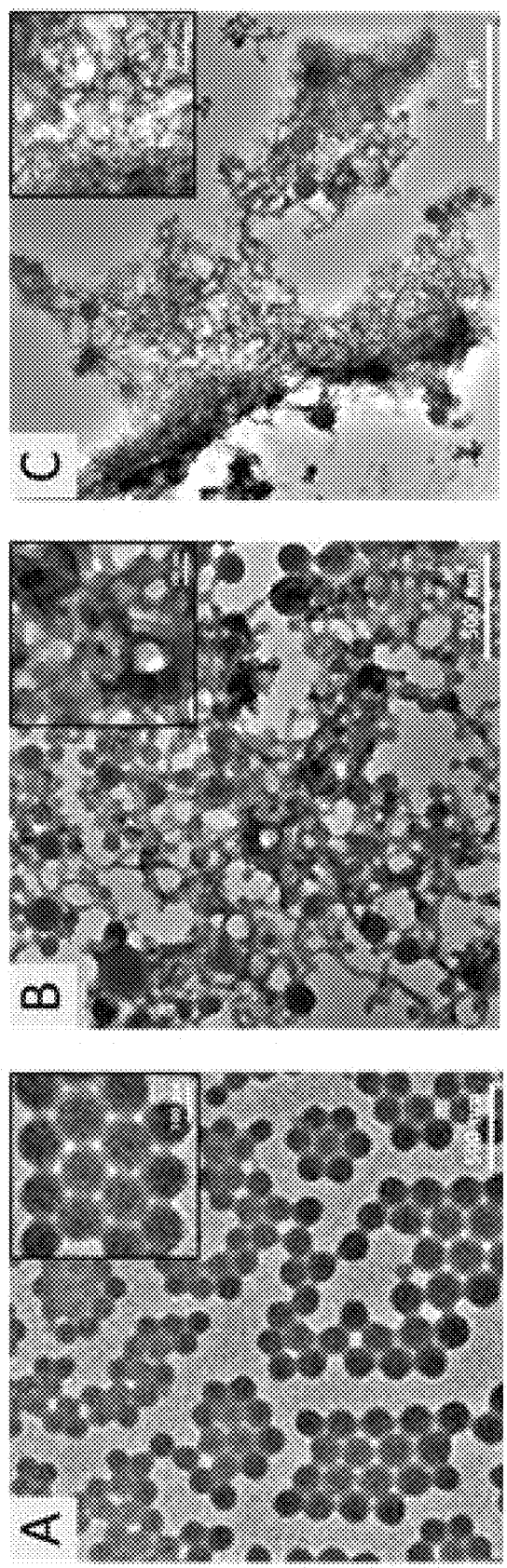

FIG. 15(a) shows that the size of D-FNP2 increased by about 378 nm to 1 μm, respectively, after 1 to 3 hours after $H_2O_2$ treatment. $H_2O_2$ may rapidly diffuse through a carboxyl shell of nanoparticles and oxidize a ferrocene core to ferrocenium. Micelles may swell due to its high hydrophilicity, and even π-π stacking effects may break immediately due to static electricity between ferrocenium ions. In addition, when a surface charge of D-FNP2 is dramatically reduced to form positively charged ferrocene ($Fe^{3+}$) in the ferrocene group of D-FNP2, a negative surface charge may decrease (FIG. 15(b)). In order to visualize the sensitivity of D-FNP2 to oxidation and reduction (redox), TEM images of D-FNP2 before and after oxidation through $H_2O_2$ treatment were compared. Referring to FIG. 15(c), after oxidation proceeded for 2 hours, an enlarged shape of the expanded D-FNP2 was observed. At 4 hours after oxidation, a broken fragment of D-FNP2 was clearly identified.

Analysis Results on Cytotoxicity of Ferrocene Nanoparticles

Figure 16:
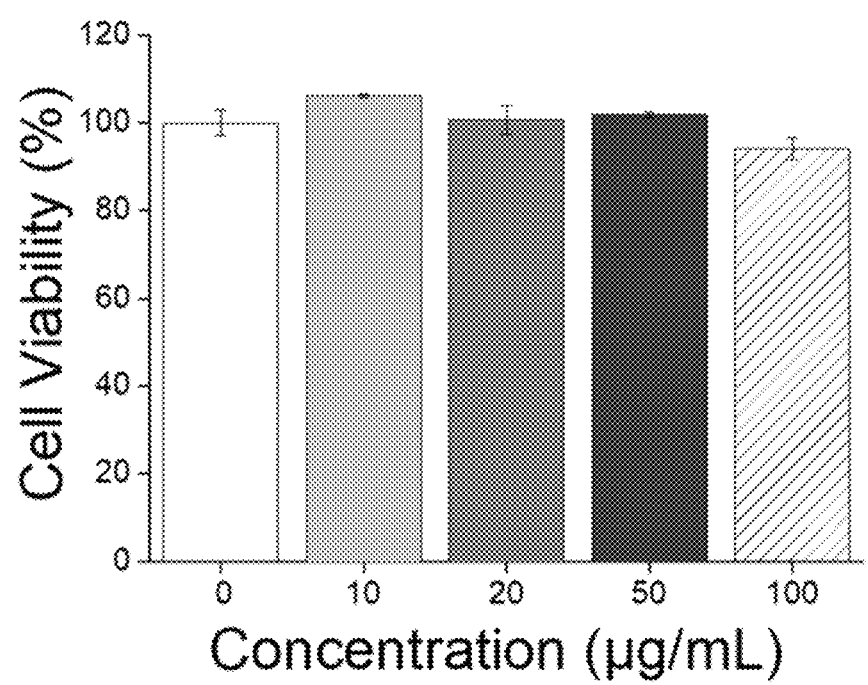
FIG. 16 illustrates results of cytotoxicity analysis of ferrocene nanoparticles according to an embodiment.

In order to identify biocompatibility of D-FNP2, cytotoxicity of D-FNP2 was evaluated using NIH 3T3 fibroblasts (FIG. 16). Cell viability was analyzed by MTT analysis after nanoparticle treatment.

Referring to FIG. 16, it was appreciated that cell viability was not significantly affected by D-FNP2 at a concentration ranging from 0 to 100 μg/mL. These results imply that ROS-sensitive D-FNP2 has excellent biocompatibility and thus is suitable for various biomedical applications.

Accordingly, in order to overcome the limitations of the conventional method of preparing ferrocene nanoparticles, it was possible to continuously manufacture ferrocene nanoparticles at a high production rate by using the device for producing nanoparticles according to an embodiment. As compared to the B-FNP according to Comparative Example, the D-FNP according to an embodiment has smaller hydrodynamic diameter, PDI, and zeta potential. In addition, while B-FNP is poor in long-term stability due to limited dispersion stability, it is noteworthy that D-FNP2 showed significantly stable dispersion stability for 2 months even though it was prepared using a 10 mg/mL precursor solution. In addition, after lyophilizing without a cryoprotectant, D-FNPs showed high stability when redispersed. In addition, D-FNP showed high sensitivity to ROS and excellent biocompatibility. D-FNP having ROS responsiveness, uniform size control, and high stability may be used as an effective and controllable therapeutic agent for various diseases.

As set forth hereinabove, according to one or more embodiments of the present disclosure, a device for producing nanoparticles may not raise an issue of leakage of a solution when a reactant is injected into a mixer, may allow the reactant to be continuously injected into the mixer, may be safe even for highly toxic materials, and may have high reproducibility and enhanced particle uniformity because the reactants are mixed in a turbulent state.

While the present disclosure has been illustrated and described with reference to the embodiments thereof, it will be another to those of ordinary skill in the art that various changes in form and detail may be made thereto without departing from the spirit and scope according to an embodiment.

What is claimed is:

1. A device for producing nanoparticles, comprising:
    a first connector comprising a first supply tube fitting member, a second supply tube fitting member, and a first discharge tube fitting member;
    a first tube having one side connected to the first supply tube fitting member;
    a second tube having one side connected to the second supply tube fitting member;
    a first conduit having one side connected to the first discharge tube fitting member;
    a first supply connected to another side of the first tube to supply a first material to the first conduit; and
    a second supply connected to another side of the second tube to supply a second material to the first conduit,
    wherein at least a portion of the first tube or the second tube is disposed in the first connector and in the first conduit,
    wherein an outer diameter of the at least a portion of the first tube or the second tube disposed in the first conduit is smaller than an inner diameter of the first conduit,
    wherein a length of the at least a portion of the first tube or the second tube disposed in the first conduit is shorter than a length of the first conduit,
    wherein a material of the first connector, the first tube, and the second tube comprises a fluorine-based polymer,
    wherein a material of the first conduit consists of a fluorine-based polymer, and
    wherein the produced nanoparticles are reactive oxygen species (ROS)-reactive drug delivery nanoparticles.

2. The device for producing nanoparticles of claim 1, wherein the first supply or the second supply is a diaphragm pump.

3. The device for producing nanoparticles of claim 1, wherein the first connector further includes a third supply tube fitting member, and
the device for producing nanoparticles further comprises:
    a third tube having one side connected to the third supply tube fitting member; and
    a third supply connected to another side of the third tube to supply a third material to the first conduit.

4. The device for producing nanoparticles of claim 1, further comprising:
    a second connector comprising a connection tube fitting member, a fourth supply tube fitting member, and a second discharge tube fitting member;
    the first conduit having one side connected to the connection tube fitting member;
    a fourth tube having one side connected to the fourth supply tube fitting member;
    a second conduit having one side connected to the second discharge tube fitting member; and
    a fourth supply connected to another side of the fourth tube to supply a fourth material to the second conduit,
    wherein a material of the second connector, the fourth tube, and the second conduit comprises a fluorine-based polymer.

5. The device for producing nanoparticles of claim 1, wherein the first supply supplies the first material to the first conduit to form turbulence at an end portion of the at least a portion of the first tube in the first conduit, or the second supply supplies the second material to the first conduit to form turbulence at an end portion of the at least a portion of the second tube in the first conduit.

6. The device for producing nanoparticles of claim 1, wherein the first material and the second material are mixed while forming turbulence in the first conduit.

7. The device for producing nanoparticles of claim 6, wherein a Reynolds number of a solution flow of a mixture of the first material and the second material is 800 or more.

8. The device for producing nanoparticles of claim 1, wherein the nanoparticles formed by the device for producing nanoparticles are formed at a rate of 20 mg/min or more.

9. The device for producing nanoparticles of claim 1, wherein the first material comprises a nano-precursor, and the second material comprises a non-solvent.

10. The device for producing nanoparticles of claim 3, wherein the third material comprises a nano-precursor, a non-solvent, a quenching material, or a surfactant.

\* \* \* \* \*